(12) United States Patent
Sugio et al.

(10) Patent No.: US 8,419,654 B2
(45) Date of Patent: Apr. 16, 2013

(54) EYE GAZE TRACKING APPARATUS, IMAGING APPARATUS, EYE GAZE TRACKING METHOD, PROGRAM, AND INTEGRATED CIRCUIT

(75) Inventors: Toshiyasu Sugio, Osaka (JP); Daisuke Sato, Osaka (JP)

(73) Assignee: Panasonic Corporation, Osaka (JP)

(*) Notice: Subject to any disclaimer, the term of this patent is extended or adjusted under 35 U.S.C. 154(b) by 541 days.

(21) Appl. No.: 12/669,644

(22) PCT Filed: May 20, 2009

(86) PCT No.: PCT/JP2009/002220
§ 371 (c)(1),
(2), (4) Date: Jan. 19, 2010

(87) PCT Pub. No.: WO2009/142008
PCT Pub. Date: Nov. 26, 2009

(65) Prior Publication Data
US 2010/0204608 A1    Aug. 12, 2010

(30) Foreign Application Priority Data

May 20, 2008 (JP) ................................ 2008-131506
Jun. 20, 2008 (JP) ................................ 2008-161328
Jun. 20, 2008 (JP) ................................ 2008-161329

(51) Int. Cl.
*A61B 13/00* (2006.01)
*A61B 5/103* (2006.01)
*A61B 5/117* (2006.01)
*A61B 3/14* (2006.01)

(52) U.S. Cl.
USPC ............ 600/558; 600/595; 351/206; 351/209

(58) Field of Classification Search .................. 600/558, 600/595; 382/117; 351/206, 209
See application file for complete search history.

(56) References Cited

U.S. PATENT DOCUMENTS 5,360,971 A * 11/1994 Kaufman et al. ............. 250/221

FOREIGN PATENT DOCUMENTS

| JP | 9-34631 | 2/1997 |
| JP | 2615831 | 6/1997 |
| JP | 11-85384 | 3/1999 |

(Continued)

OTHER PUBLICATIONS

International Search Report issued Jun. 16, 2009 in International (PCT) Application No. PCT/JP2009/002220.
Hiroyuki Manabe et al., "*Headphone shaped eye-gaze interface*", NTT DoCoMo Multimedia Laboratories, Interaction 2006, Mar. 2, 2006 with partial English translation (p. 2, Lines 5-14).

*Primary Examiner* — Sean P Dougherty
*Assistant Examiner* — Devin Henson
(74) *Attorney, Agent, or Firm* — Wenderoth, Lind & Ponack, L.L.P.

(57) ABSTRACT

An eye gaze tracking apparatus (100) includes: an electro-oculogram measuring unit that outputs an electro-oculogram original signal; a calibration index presenting unit (103) that presents a calibration index to a user; a saccade detection unit (104) that outputs an electro-oculogram change amount that is an amount of change in an electro-oculogram before or after a saccadic movement which is measured when a gaze-path position of the user moves to the calibration index; a calibration parameter calculating unit (105) that calculates a calibration parameter based on a position of the calibration index and an electro-oculogram change amount; and a calibration unit (101) that detects the gaze-path direction of the user from the electro-oculogram original signal.

13 Claims, 38 Drawing Sheets

FOREIGN PATENT DOCUMENTS

| | | |
|---|---|---|
| JP | 11-276461 | 10/1999 |
| JP | 2002-272693 | 9/2002 |
| JP | 2007-252879 | 10/2007 |
| WO | 2006/106877 | 10/2006 |

* cited by examiner

FIG. 2A

| Electro-oculogram change amount | Eye ball movement angle |
|---|---|
| 5V | 40° |
| 4.5V | 30° |
| 4V | 20° |
| ... | ... |
| -5V | -40° |

FIG. 2B

| Electro-oculogram change amount | Gaze-point |
|---|---|
| 5V | (600,0) |
| 4.5V | (500,0) |
| 4V | (400,0) |
| ... | ... |
| -5V | (-600,0) |

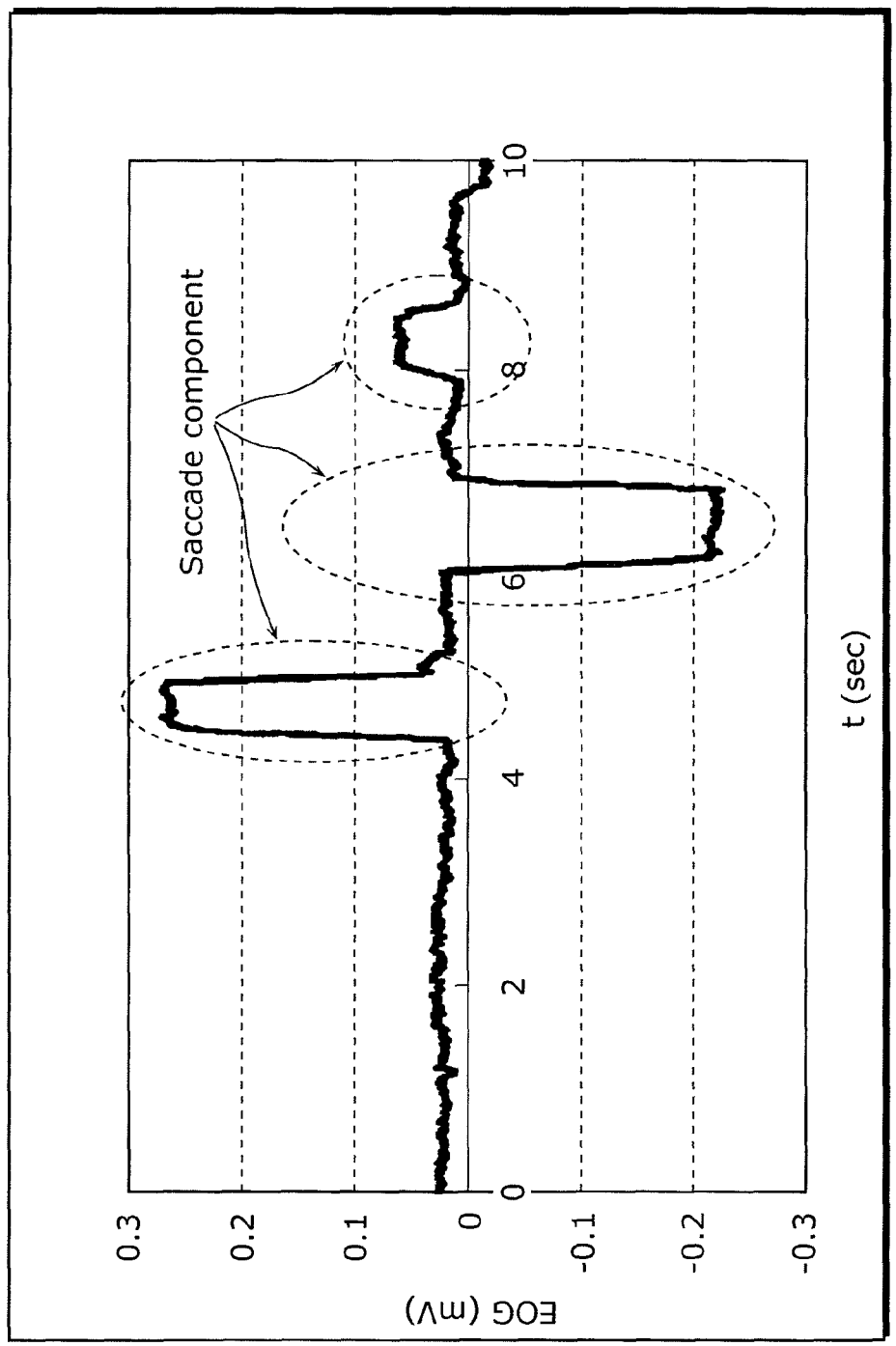

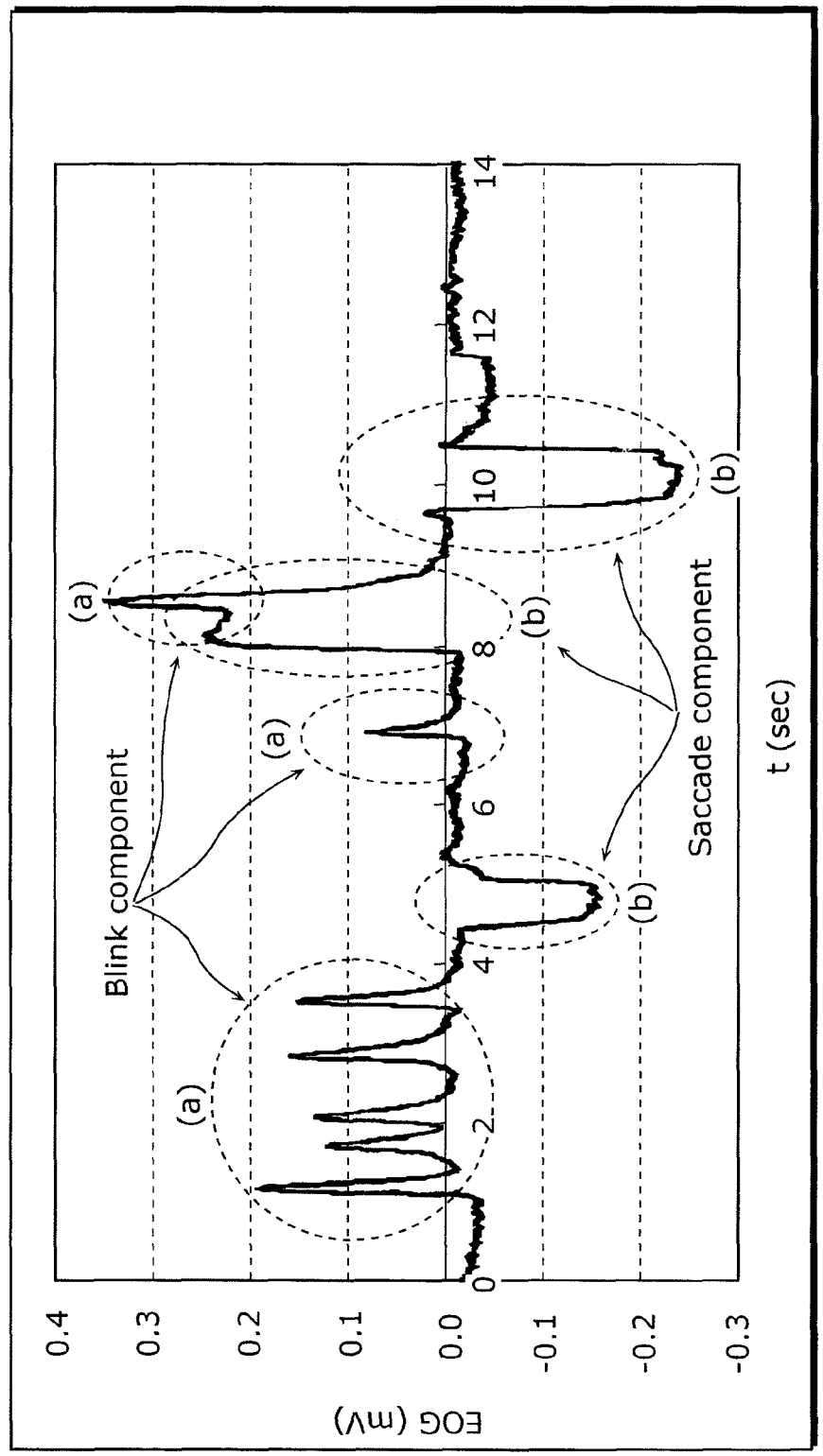

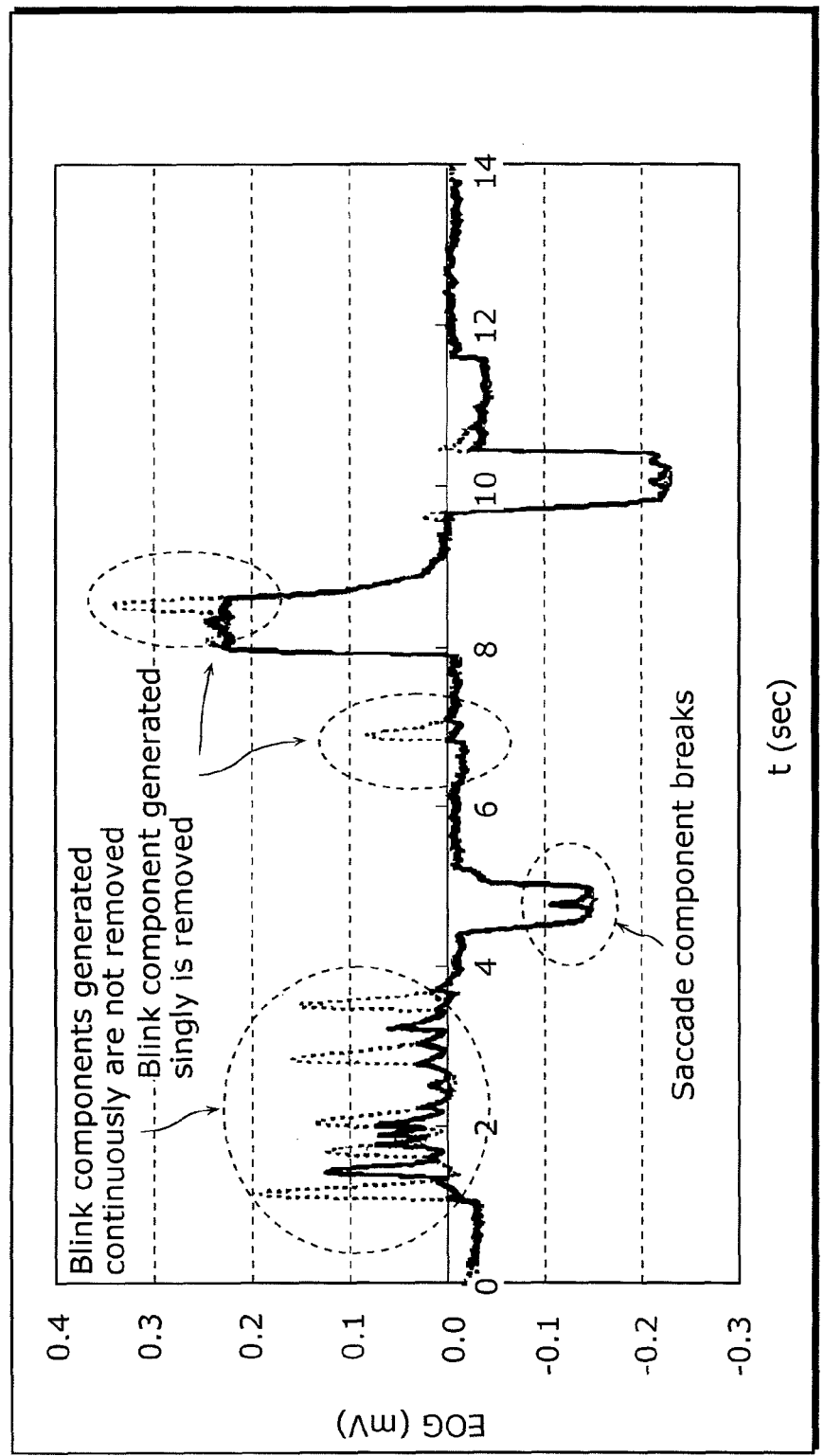

EYE GAZE TRACKING APPARATUS, IMAGING APPARATUS, EYE GAZE TRACKING METHOD, PROGRAM, AND INTEGRATED CIRCUIT

TECHNICAL FIELD

The present invention relates to an eye gaze tracking apparatus which, when calculating a gaze-point of a user using an electro-oculogram of the user, calibrates the electro-oculogram and the gaze-point without affected by a drift.

BACKGROUND ART

In recent years, there have been presented gaze-path input interfaces and the like which utilizes an eye movement of a human. Methods for detecting an eye movement includes: an EOG that utilizes a potential generated between a cornea and a retina; a corneal reflex method that detects a movement of a virtual image generated inside a cornea by irradiating a spot-light on an eyeball; a strong-reflection method that uses a difference in reflectance between the cornea and the retina; a method using contact lenses; and so on.

Here, the EOG is a method for detecting an eye movement that utilizes the fact that a human cornea is charged positively with respect to the retina. More specifically, electrodes are placed near a human eyeball and a change in a potential measured by the electrodes is used to detect the eye movement. FIG. 36A and FIG. 36B show examples of the method for detecting an eye movement which utilizes the EOG. FIG. 36A and FIG. 36B are examples of the case where an electrode is placed to the outside and the inside of the right eye of a user at the same distance away from the center of the eyeball.

Assuming the electro-oculogram generated on the outside electrode A is Va and the electro-oculogram generated on the inside electrode B is Vb, Va and Vb are equal when the eyeball of the user is positioned at the center as in FIG. 36A, and the electro-oculogram $V_{a-b}$ measured becomes 0V. On the other hand, in the case where the user looks to the right as in FIG. 36B, the electrode A becomes closer to the cornea of the right eye, and thus Va becomes greater than Vb and the measured electro-oculogram $V_{a-b}$ indicates a plus value. Conversely, in the case where the user looks to the left, Va becomes smaller than Vb and the measured electro-oculogram $V_{a-b}$ indicates a minus value. Thus, it can be observed that the user has moved the eye, to the right when the measured electro-oculogram $V_{a-b}$ indicates the plus value, and to the left when the measured electro-oculogram $V_{a-b}$ indicates the minus value. In the EOG method, an eye movement of a user is detected by utilizing such changes in the measured electro-oculogram $V_{a-b}$ as described above.

When identifying the gaze-point of a user by detecting an eye movement with use of the EOG, it is necessary to calibrate an electro-oculogram that has been generated and the gaze-point of the user at the time. An example of methods for calibrating the gaze-point of a user and a generated electro-oculogram in a real space includes techniques described in Patent Literature 1 and Patent Literature 2 as described below.

With the calibration method disclosed by the Patent Literature 1, an arbitrary calibration pattern is displayed on a display at the time of calibration. Then, data on eye movements in a horizontal and a vertical direction at the time when a user sees the calibration pattern is obtained, and a calibration coefficient is obtained using the data. A method for obtaining the eye movement data includes: a method using corneal reflex; a method using a difference in reflectance between the cornea and a retina; a method using contact lenses; the so EOG that utilizes a potential generated between the cornea and the retina, or the like.

With the calibration method disclosed by the Patent Literature 2, an electro-oculogram of a user is detected, and a mouse cursor on a display is operated by using the detected electro-oculogram. A sight index is displayed sequentially at various positions on the display and a user gazes the sight index to measure the electro-oculogram at this time. Then, the result of this measurement is used for calibration.

CITATION LIST

Patent Literature

[Patent Literature 1]
Japanese Patent No. 2615831
[Patent Literature 2]
Japanese Unexamined Patent Application Publication No. 11-85384

SUMMARY OF INVENTION

Technical Problem

In the Patent Literature 1 and the Patent Literature 2, a calibration index displayed on the display and an electro-oculogram generated when gazing the calibration index are used to calculate a calibration parameter, thereby calibrating the electro-oculogram and the gaze-point. However, when measuring the electro-oculogram, a phenomenon called a drift occurs. A drift is a phenomenon in which a base line of an electro-oculogram changes temporally, and materials of an electrode used for measuring the electro-oculogram, a change in contact between a skin and the electrode, and so on are considered as a factor for the phenomenon.

FIG. 37 shows a result of measuring an electro-oculogram by actually placing an electrode on a user. FIG. 37 is a result of measuring an electro-oculogram when plural indexes are displayed in one second in the order shown in FIG. 38. Referring to FIG. 37, it can be seen that a base line of the electro-oculogram changes with time. More specifically, the electro-oculogram changes also when gazing the index (R4) due to a drift. When the calibration methods as in the Patent Literature 1 and the Patent Literature 2 are applied in a situation where such a drift occurs, there is a problem that calibration cannot be carried out properly, because the electro-oculogram changes even when gazing one point.

The present invention has been conceived to solve the above problem, and aims to provide an eye gaze tracking apparatus that properly calibrates an electro-oculogram and a gaze-point of a user.

Solution to Problem

An eye gaze tracking apparatus according to an aspect of the present invention detects a gaze-path direction of a user from an electro-oculogram. More specifically, the eye gaze tracking apparatus includes: an electro-oculogram measuring unit configured to measure the electro-oculogram resulting from an eye movement, and to output an electro-oculogram original signal; a calibration index presenting unit configured to present a calibration index to the user; a saccade detection unit configured to detect a saccadic movement from the electro-oculogram original signal, and to output an electro-oculogram change amount, the saccadic movement being a rapid eyeball movement which occurs when a gaze-point of the user moves to the calibration index presented by the calibration index presenting unit, and the electro-oculogram change amount being an amount of change in the electro-oculogram before or after the saccadic movement; a calibration parameter calculating unit configured to calculate a calibration parameter based on a position of the calibration index presented by the calibration index presenting unit and the electro-oculogram change amount that has been output from the saccade detection unit; and a calibration unit configured to detect the gaze-path direction of the user from the electro-oculogram original signal based on the calibration parameter.

It is possible to obtain an appropriate calibration parameter from which an effect of a drift is eliminated, by calculating the calibration parameter based on the amount of change in the electro-oculogram before or after a saccadic movement as in the above-described structure.

Further, the saccade detection unit may include: a delay signal generation unit configured to delay the electro-oculogram original signal for a predetermined amount of time and output a delay signal; a subtraction unit configured to generate an output signal obtained by subtracting the delay signal from the electro-oculogram original signal; and a saccade determining unit configured to determine that a signal exceeding a predetermined threshold in the output signal is a saccade signal that indicates the saccadic movement.

This makes it possible to detect a saccade signal with a sign (information representing a moving direction of an eyeball).

Further, the predetermined amount of time of the delay may be smaller than an amount of time of fixation by the user on the calibration index. This makes it possible to prevent a break of a saccade waveform.

Further, the saccade detection unit may include: a first filtering unit configured to output a first electro-oculogram signal by performing one of maximum value filtering and minimum value filtering, on the electro-oculogram original signal; a subtraction unit configured to subtract one of the first electro-oculogram signal and a second electro-oculogram signal from the other, the second electro-oculogram signal being obtained from the electro-oculogram original signal; and a saccade determining unit configured to determine that a signal exceeding a predetermined threshold among the output signals is a saccade signal that indicates the saccadic movement.

The above structure also makes it possible to detect a saccade signal. It is to be noted that, the above-described "the second electro-oculogram signal" is an electro-oculogram signal that is obtained directly or indirectly from an electro-oculogram original signal, and may also be the electro-oculogram original signal itself.

The saccade detection unit may further include a second filtering unit configured to output the second electro-oculogram signal by performing the other one of the maximum value filtering and the minimum value filtering, on the electro-oculogram original signal. This makes it possible to easily obtain a saccade signal that includes a generation time of the saccade signal.

Further, the saccade detection unit may further include a second filtering unit configured to output the second electro-oculogram signal by performing the other one of the maximum value filtering and the minimum value filtering, on the first electro-oculogram signal. This makes it possible to remove a blink signal and detect a saccade signal.

Further, the calibration index presenting unit is configured to present a first calibration index to the user in response to receiving a calibration parameter update instruction, and then present a second calibration index at a position different from a position of the first calibration index in response to the detection of the saccadic movement by said saccade detection unit. And the saccade detection unit may output, to said calibration parameter calculating unit, the electro-oculogram change amount which is measured when the gaze-point of the user moves from the first calibration index to the second calibration index. This makes it possible to calculate an appropriate calibration parameter while eliminating the effect of a drift.

Further, the calibration parameter calculating unit may determine, as the calibration parameter, a value resulting from dividing the electro-oculogram change amount that has been output from the saccade detection unit, by an eyeball movement angle which is measured when the gaze-point of the user moves from the first calibration index to the second calibration index. Further, the calibration parameter may be a table holding a plurality of combinations of an eyeball movement angle which is measured when the gaze-point of the user moves from the first calibration index to the second calibration index and the electro-oculogram change amount that corresponds to the eyeball movement angle. It is possible to detect the gaze-path direction using the electro-oculogram and the calibration parameter according to any of the above-described methods.

An imaging apparatus according to an aspect of the present invention performs imaging in a gaze-path direction of a user. More specifically, the imaging apparatus includes: an imaging unit; an eye gaze tracking apparatus described above; and an image control unit configured to cause the imaging unit to image a gaze-path direction detected by the calibration unit. This makes it possible to change the orientation of the imaging unit according to the movement of a gaze-path of a user.

With an eye gaze tracking method according to an aspect of the present invention, a gaze-path direction of a user is detected. To be specific, the eye gaze tracking method including: measuring an electro-oculogram resulting from an eye movement, and outputting an electro-oculogram original signal; presenting a calibration index to the user; detecting a saccadic movement from the electro-oculogram original signal, and outputting an electro-oculogram change amount, the saccadic movement being a rapid eyeball movement which occurs when a gaze-point of the user moves to the calibration index presented in the presenting a calibration index, and the electro-oculogram change amount being an amount of change in the electro-oculogram before or after the saccadic movement; calculating a calibration parameter based on a position of the calibration index presented in the presenting a calibration index and the electro-oculogram change amount that has been output in the detecting a saccadic movement; and detecting the gaze-path direction of the user from the electro-oculogram original signal based on the calibration parameter.

A program according to an aspect of the present invention causes a computer to detect a gaze-path direction of a user, the computer being connected to an electro-oculogram measuring unit that measures an electro-oculogram resulting from an eye movement and outputs an electro-oculogram original signal. To be specific, the program includes: presenting a calibration index to the user; detecting a saccadic movement from the electro-oculogram original signal, and outputting an electro-oculogram change amount, the saccadic movement being a rapid eyeball movement which occurs when a gaze-point of the user moves to the calibration index presented in said presenting a calibration index, and the electro-oculogram change amount being an amount of change in the electro-oculogram before or after the saccadic movement; calculating a calibration parameter based on a position of the calibration index presented in said presenting a calibration index and the electro-oculogram change amount that has been output in said detecting a saccadic movement; and detecting the gaze-path direction of the user from the electro-oculogram original signal based on the calibration parameter.

An integrated circuit according to an aspect of the present invention detects a gaze-path direction of a user and is connected to an electro-oculogram measuring unit that measures an electro-oculogram resulting from an eye movement and outputs an electro-oculogram original signal. To be specific, the integrated circuit includes: a calibration index presenting unit configured to present a calibration index to the user; a saccade detection unit configured to detect a saccadic movement from the electro-oculogram original signal, and to output an electro-oculogram change amount, the saccadic movement being a rapid eyeball movement which occurs when a gaze-point of the user moves to the calibration index presented by the calibration index presenting unit, and the electro-oculogram change amount being an amount of change in the electro-oculogram before or after the saccadic movement; a calibration parameter calculating unit configured to calculate a calibration parameter based on a position of the calibration index presented by the calibration index presenting unit and the electro-oculogram change amount that has been output from the saccade detection unit; and a calibration unit configured to detect the gaze-path direction of the user from the electro-oculogram original signal based on the calibration parameter.

It is to be noted that, the present invention can be embodied not only as an eye gaze tracking apparatus and an imaging apparatus, but also as an integrated circuit that implements functions of the eye gaze tracking apparatus and the imaging apparatus, or a program which, when loaded into a computer, allows a computer to execute the functions. In addition, such a program may be distributed, of course, via recording medium such as a CD-ROM and communication medium such as the Internet.

Advantageous Effects of Invention

According to the present invention, since a calibration parameter is calculated based on an electro-oculogram change amount that is an amount of change in the electro-oculogram before or after a saccadic movement, it is possible to obtain an eye gaze tracking apparatus that is capable of obtaining an appropriate calibration parameter from which an effect of a drift is eliminated.
(Further Information about Technical Background to this Application)

The disclosure of Japanese Patent Application No. 2008-131506 filed on May 20, 2008, Japanese Patent Application No. 2008-161328 filed on Jun. 20, 2008, and Japanese Patent Application No. 2008-161329 filed on Jun. 20, 2008, including specification, drawings and claims are incorporated herein by reference in its entirety.

BRIEF DESCRIPTION OF DRAWINGS

FIG. 2A is an example of a calibration parameter, and is a diagram which shows a table holding plural combinations of an electro-oculogram change amount and an eyeball movement angle associated with each other.

FIG. 2B is another example of the calibration parameter, and is a diagram shows a table holding plural combinations of an electro-oculogram change amount and a gaze-point associated with each other.

FIG. 3 is a diagram which shows an example of an electro-oculogram signal that includes a saccade signal.

FIG. 21 is a diagram that shows an example of an electro-oculogram signal that includes a blink signal.

FIG. 22 is a diagram that shows an electro-oculogram signal obtained by applying a median filter processing on the electro-oculogram signal of FIG. 21.

DESCRIPTION OF EMBODIMENTS

Embodiments according to the present invention will be described below with reference to the drawings. It is to be noted that each embodiment described below may be combined with other embodiment in an arbitrary combination unless an advantageous effect of the present invention is diminished due to the combination.

Embodiment 1

Figure 1:
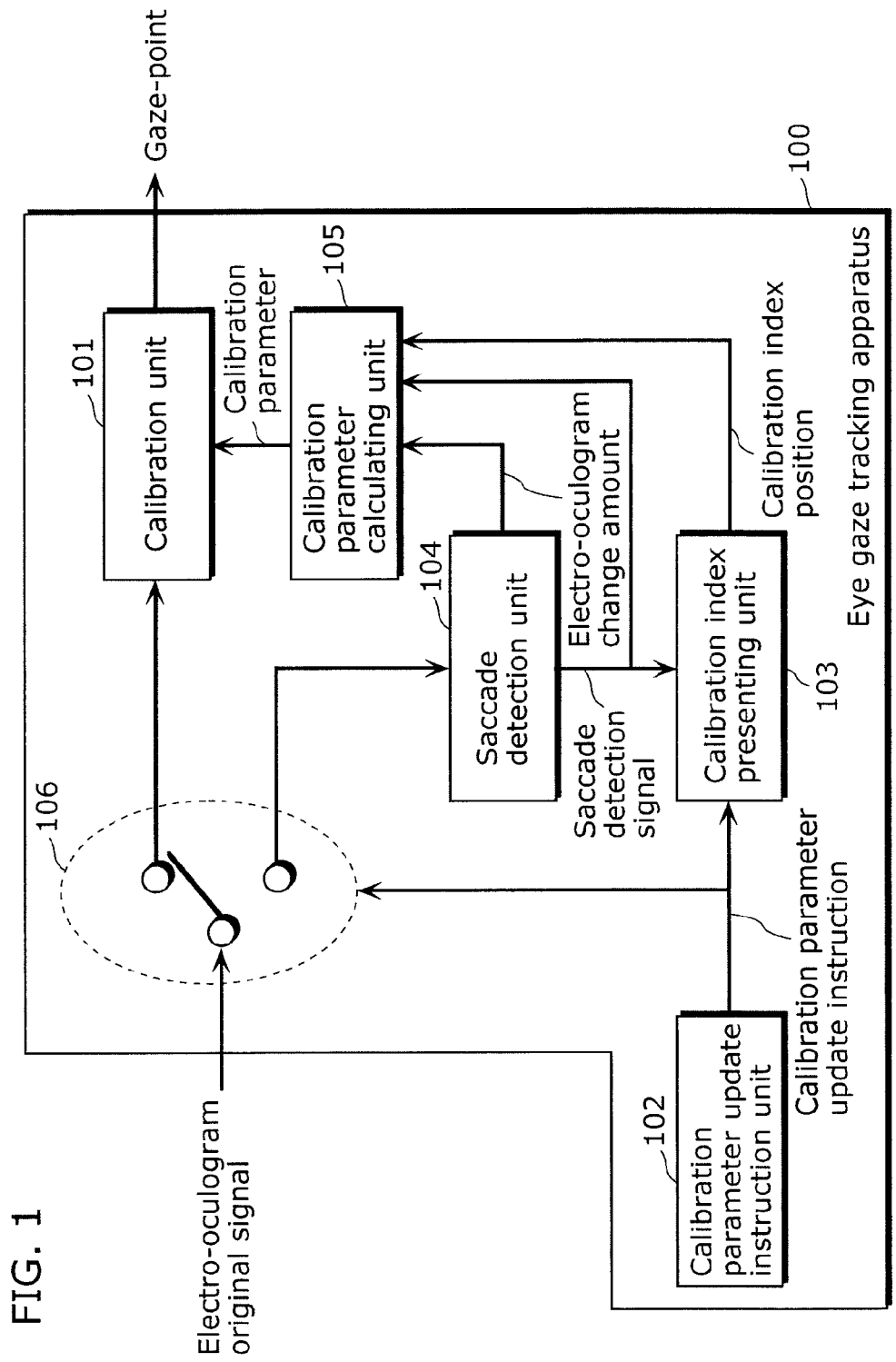
FIG. 1 is a block diagram of an eye gaze tracking apparatus according to an Embodiment 1.

FIG. 1 is a block diagram that shows a structure of an eye gaze tracking apparatus 100 according to Embodiment 1 of the present invention. The eye gaze tracking apparatus 100 as shown in FIG. 1 includes: an electro-oculogram measuring unit (illustration omitted) placed around a user's eye to measure an electro-oculogram and output an electro-oculogram original signal; a calibration unit 101 that converts the electro-oculogram original signal into a gaze-point (hereinafter, can also be referred to as "gaze path direction"); a calibration parameter update instruction unit 102 that instructs update of a calibration parameter; a calibration index presenting unit 103 that presents a calibration index in response to the calibration parameter update instruction; a saccade detection unit 104 that detects a saccade signal from the electro-oculogram original signal; a calibration parameter calculating unit 105 that calculates a calibration parameter based on an electro-oculogram change amount output from the saccade detection unit 104 and a position of the calibration index output from the calibration index presenting unit 103; and a switch 106 that switches output destinations of the electro-oculogram original signal between the calibration unit 101 and the saccade detection unit 104.

Figure 36:
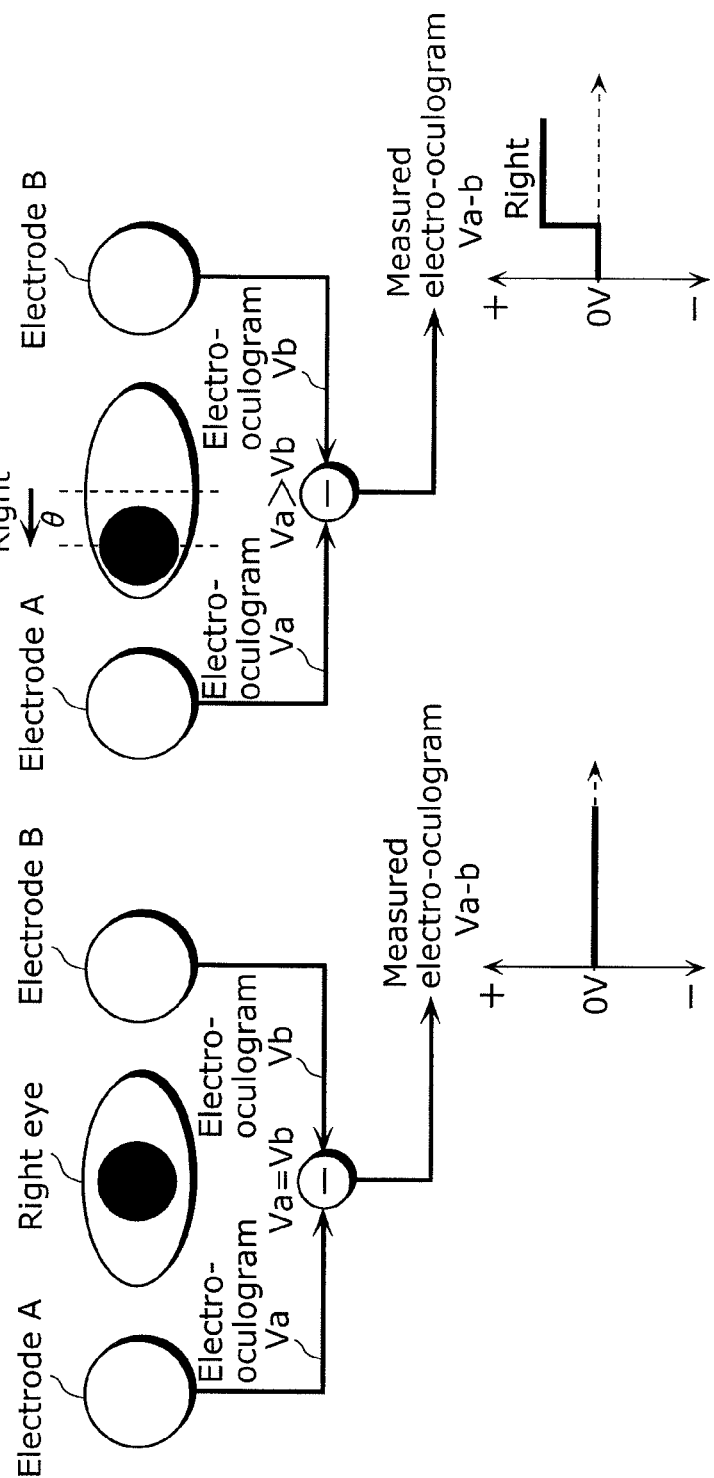
FIG. 36A is a diagram which explains the EOG and shows a user's eyeball facing front.
FIG. 36B is a diagram which explains the EOG and shows a user's eyeball facing right.
Figure 37:
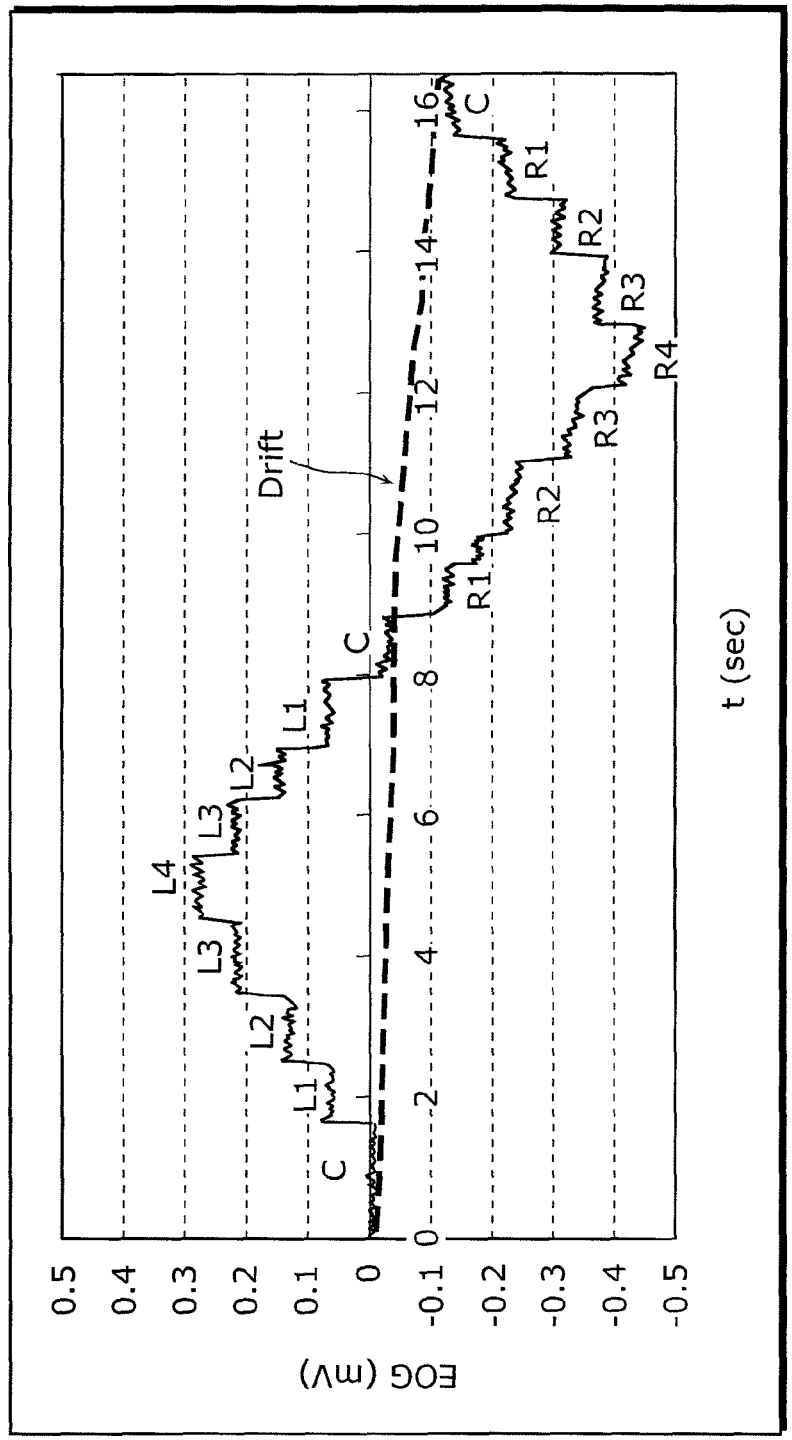
FIG. 37 is a diagram that shows an example of a drift in measuring an electro-oculogram.
Figure 38:
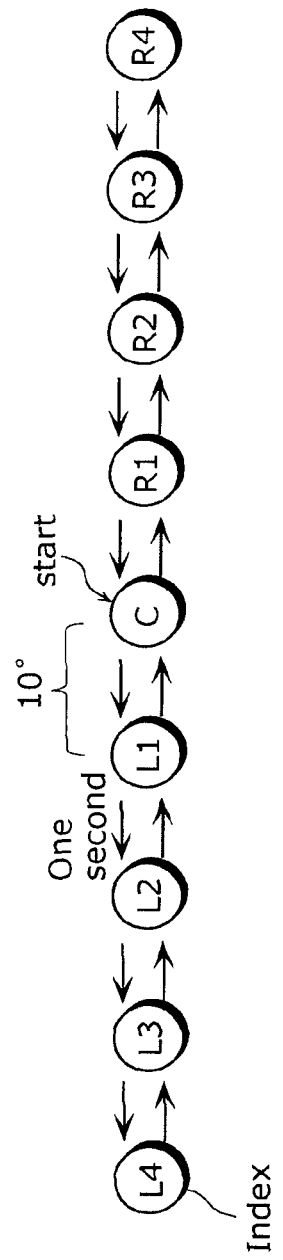
FIG. 38 is a diagram for explaining a drift in measuring an electro-oculogram.

The electro-oculogram measuring unit is, typically, an electrode that is placed around an eye of a user. The placing method is not specifically limited. For example, an electrode A placed at the outer corner of the eye may be used in combination with an electrode B placed at the inner corner of the eye, as shown in FIG. 36A and FIG. 36B. Or, an electrode may be placed on one or both of above and under an eye as shown in FIG. 20A to FIG. 20D. Further, an electrode may be placed on above and under a temple.

The calibration unit 101 calculates a gaze-point of a user from the electro-oculogram original signal by using a calibration parameter held in advance. Here, the calibration parameter is a parameter for converting the electro-oculogram original signal into an eyeball movement angle. One of the parameters is a calibration coefficient $\alpha$ that is used in Expression 1 indicated below.

It is generally known that a measured electro-oculogram $V_{a\text{-}b}$ changes linearly when the eyeball movement angle $\theta$ is within a certain range. Therefore, the measured electro-oculogram $V_{a\text{-}b}$ can be approximated by the following expression 1 using the calibration coefficient $\alpha$ and the eyeball movement angle $\theta$.

[Math. 1]

$$V_{a\text{-}b} = \alpha \times \theta \qquad \text{(Expression 1)}$$

An example of operations of calibration using the EOG will be described. In the case where an electro-oculogram Ve will be input, as an electro-oculogram original signal, into the calibration unit 101, an eyeball movement angle $\theta$ is calculated by using the expression 1. Then, a gaze-point is obtained from the moved angle $\theta$ by using information such as a distance between the user and the gaze object. Through the above-described procedures, the gaze-point can be obtained from the electro-oculogram. It is to be noted that, the method of measuring a distance between a user and a gaze object is not specifically limited, and a distance measuring sensor and the like may be used, for example.

It is to be noted that, the present invention is not limited to the calibration method using the expression 1, and a table that holds plural combinations of the electro-oculogram change amount and the eyeball movement angle associated with each other as shown in FIG. 2A may be used as a calibration parameter. In addition, a table that holds plural combinations of the electro-oculogram and the gaze-point such as a display coordinate, a camera coordinate, and the like associated with each other as shown in FIG. 2B may be used as a calibration parameter.

The calibration parameter update instruction unit 102 outputs a calibration parameter update instruction signal to the calibration index presenting unit 103 and the switch 106 in the case where an event such as an outset of eye gaze tracking occurs. Then, when ending the update of the calibration parameter, the calibration parameter update instruction unit 102 stops outputting the calibration parameter update instruction signal.

The switch 106 switches between the calibration unit 101 and the saccade detection unit 104 for transmitting the electro-oculogram original signal, according to the calibration parameter update instruction.

The saccade detection unit 104 detects a saccade signal from the electro-oculogram original signal and uses the detected saccade signal to calculate an amount of change in the electro-oculogram at the occurrence of a saccade. a saccade (saccadic eye movement) is an eye movement that occurs due to capturing an object projected on a peripheral retina where resolution is low, at a central fovea of retina where resolution is high. It is known that the speed is significantly high, at 100 to 500 (°/sec).

FIG. 3 shows an example of a waveform of the electro-oculogram signal including a saccade signal. In FIG. 3, the areas surrounded by dot lines are portions that indicate a saccade. When a saccade occurs, a potential changes rapidly, retains the level for a fixed amount of time (fixation), and then returns to the original potential level. This is an example of the case where an eyeball is moved in saccade from an index A to an index B, and then moved again in saccade from the index B to the index B. In general, a human obtains information on surroundings by repeating fixation for approximately 0.3 seconds and saccade for several dozen milliseconds.

As one of the methods of detecting a saccade signal from the electro-oculogram original signal as shown in FIG. 3, there is a method of applying each of the maximum value filtering and the minimum value filtering on the electro-oculogram original signal to calculate the difference. The processing will be described later in detail.

Figure 4:
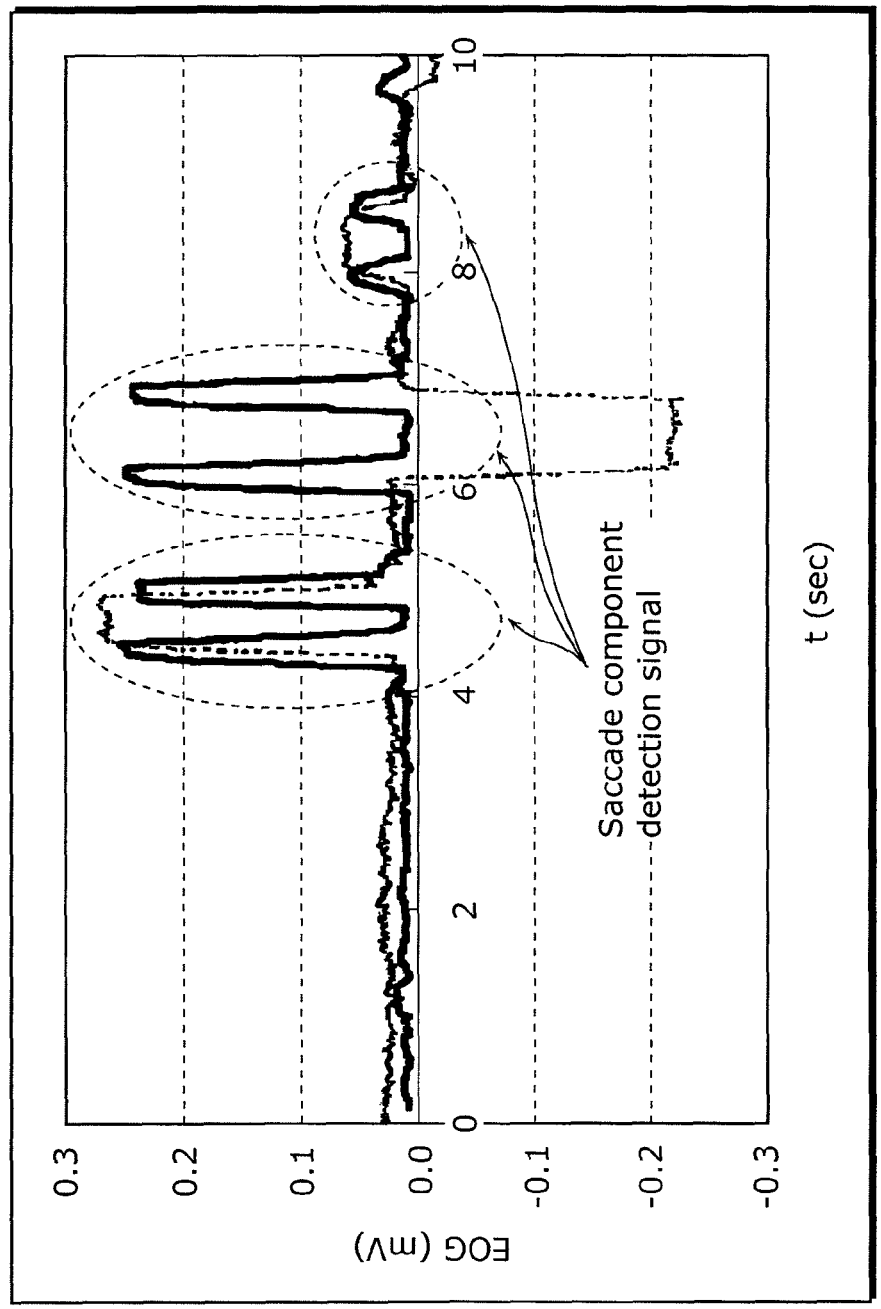
FIG. 4 is a diagram for explaining a saccade detection signal extracted from the electro-oculogram signal of FIG. 3.

FIG. 4 shows an output signal obtained by applying the maximum value filtering and the minimum value filtering on the electro-oculogram original signal shown in FIG. 3. As shown in FIG. 4, the output signal includes a peak only when the saccade occurs.

The saccade detection unit 104 further includes a saccade determination unit (illustration omitted) that determines a signal that exceeds a predetermined threshold among the output signals, as a saccade signal that indicates a saccadic movement. Then, the saccade detection unit 104 calculates an amount of change in a saccade signal (in other words, an amount of change in the electro-oculogram before or after the saccadic movement) and outputs to the calibration parameter calculating unit 105. Then, the saccade detection unit 104 outputs a saccade detection signal that indicates that the saccade signal has been detected, to the calibration index presenting unit 103 and the calibration parameter calculating unit 105.

It is to be noted that, although the minimum value filter and the maximum value filter are used as methods of detecting the saccade signal in the Embodiment 1, any techniques, such as the high pass filter and the like, may be used as long as it detects a saccade. Further, although the amount of change in the electro-oculogram that has changed during the saccade is obtained in the Embodiment 1, it may also be possible to use the amplitude of the saccade detection signal The calibration index presenting unit 103 presents a calibration index when the calibration parameter update instruction is received. Then, the calibration index presenting unit 103 changes the position of presenting the calibration index according to the saccade detection signal from the saccade detection unit 104.

Figure 5:
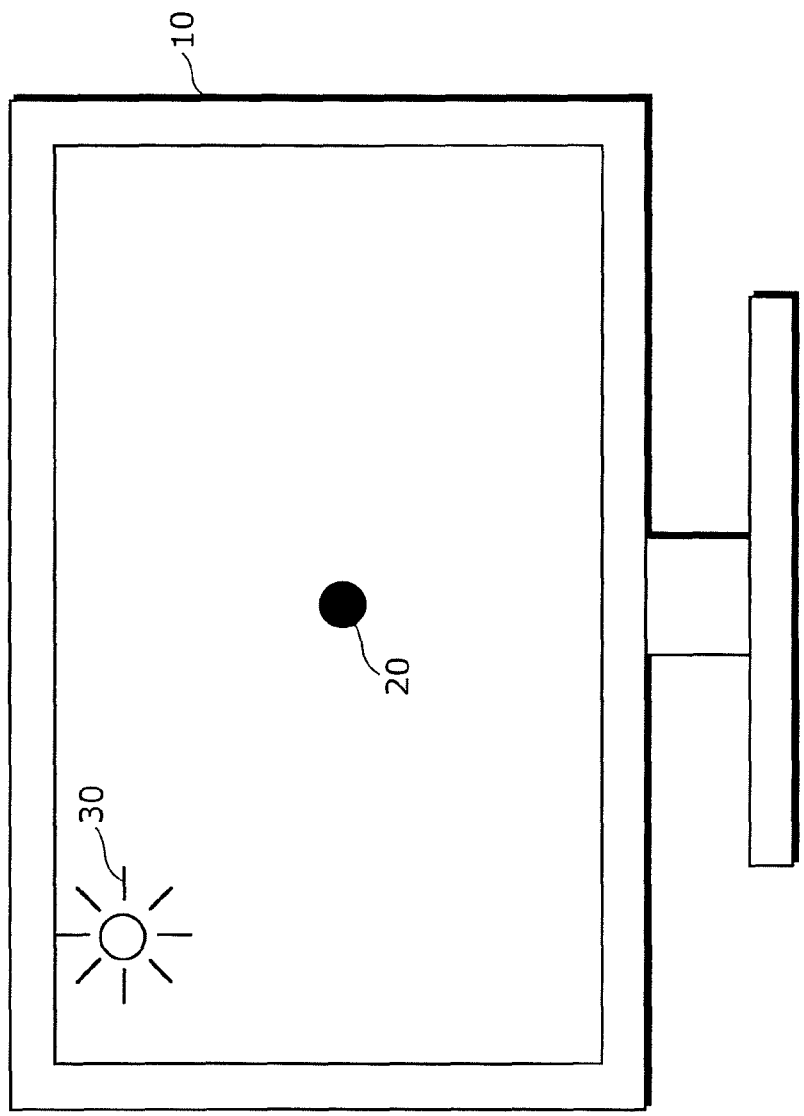
FIG. 5 is a diagram that shows a state of a display on which a calibration index is displayed.

In the case where a display 10 as shown in FIG. 5 is used to perform calibration, for example, the first calibration index 20 is displayed at the center of the display 10 in response to receiving the calibration parameter update instruction. Then, when a saccade detection signal is received, the second calibration index 30 is displayed at the upper left. Then, when a saccade detection signal is received again, the next calibration index is displayed at the upper right and the like. As described above, it is possible to induce a saccade for a user by changing the position of the calibration index according to the saccade of the user. As described above, the position of the calibration index which is changed according to the saccade of the user is output to the calibration parameter calculating unit 105.

It is to be noted that, although the first and second calibration indexes 20 and 30, respectively, are displayed on the display 10, the method of presenting the calibration index is not limited to this. For example, the calibration index may be displayed on a real space by using a laser pointer and the like.

Further, a calibration index may be selected from among objects (a human face and the like, for example) which exist in the surroundings by using a camera and so on to output audio information so that a user can recognize the calibration index. Thus, the calibration index presenting unit 103 may be any form as long as it outputs information so that a user can identify the calibration index.

The calibration parameter calculating unit 105, when the saccade detection signal is received from the saccade detection unit 104, updates a calibration parameter using the electro-oculogram change amount and the calibration index position. A calculation example of a calibration coefficient $\alpha$ that is one of calibration parameters will be described. First, an eyeball movement angle $\theta$ of a user when viewing the calibration index is calculated by using a calibration index position and distance information between the user and the object on which the calibration index is displayed (typically a display), and the like. Then, the calibration coefficient $\alpha$ can be obtained by substituting the electro-oculogram change amount Vc and the eyeball movement angle $\theta$ which have been input, into the expression 1. It is to be noted that, the method of obtaining the distance information between the user and the display is not specifically limited. For example, a distance measuring sensor or the like may be used, or the calibration parameter update instruction may be output after having a user stand at a position predetermined distance away from the display.

Figure 6:
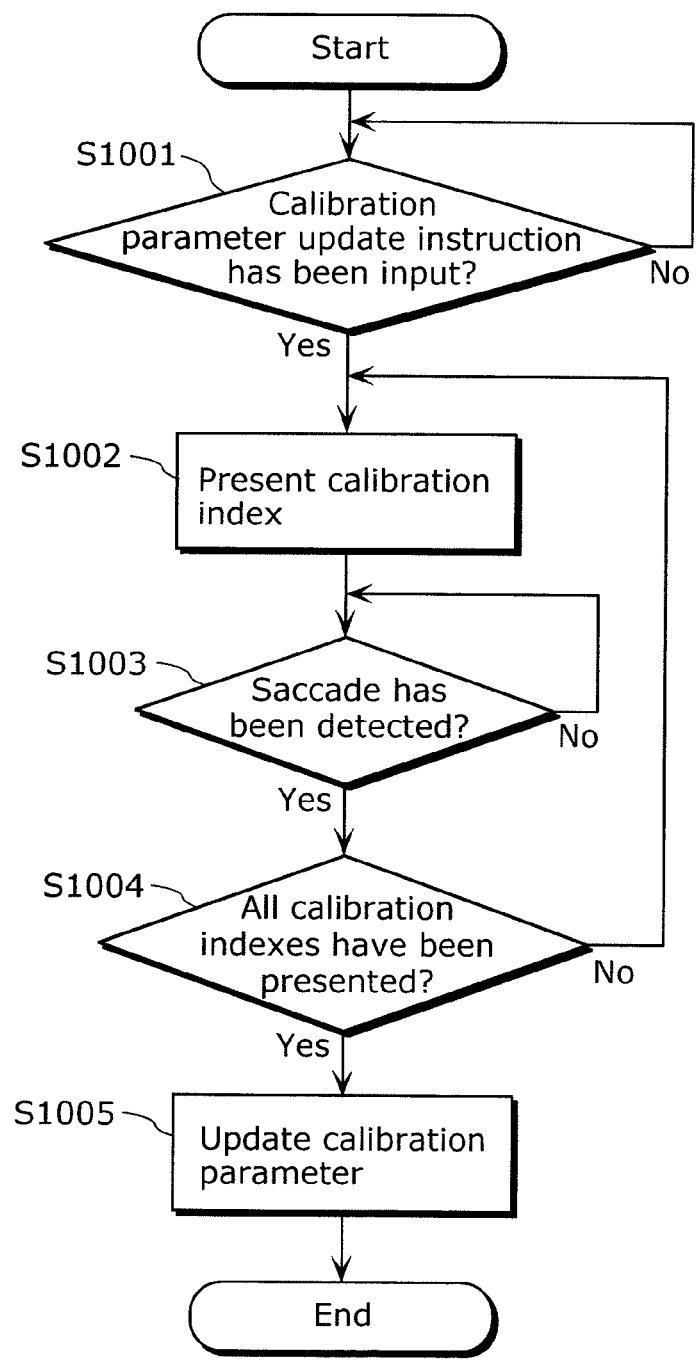
FIG. 6 is a flowchart which shows operations of the eye gaze tracking apparatus according to Embodiment 1.

Next, the procedures of updating the calibration parameter performed by the eye gaze tracking apparatus 100 according to the Embodiment 1 will be described with reference to FIG. 6. The eye gaze tracking apparatus 100 calculates a new calibration parameter when triggered by an input of a calibration parameter update instruction from outside.

First, the eye gaze tracking apparatus 100 monitors an input of the calibration parameter update instruction (S1001). The calibration parameter update instruction is transmitted from the calibration parameter update instruction unit 102 to the calibration index presenting unit 103 and the switch 106. The method of inputting the calibration parameter update instruction is not specifically limited. For example, the calibration parameter update instruction unit 102 may receive an instruction from a user or issue the instruction automatically with a predetermined timing such as the time when the power of the eye gaze tracking apparatus 100 is turned on.

Next, the calibration index presenting unit 103 which has received the calibration parameter update instruction (Yes in S1001) presents the first calibration index 20 to the user (S1002). Further, the calibration index presenting unit 103 notifies the calibration parameter calculating unit 105 of position information of the first calibration index 20. In a similar way, the switch 106 which has received the calibration parameter update instruction switches the output of the electro-oculogram original signal from the calibration unit 101 to the saccade detection unit 104.

Next, the saccade detection unit 104 monitors the electro-oculogram original signal that is input via the switch 106 to see whether or not a saccade signal is included (S1003). When the first calibration index 20 is displayed on the display 10, the gaze-path of the user moves from an arbitrary position to the first calibration index 20. At this time, a saccade signal appears.

It is to be noted that, the method of detecting a saccade signal is not specifically limited. The method includes, for example, detecting by using a maximum value filter, a minimum value filter, a delay device, and so on. The details will be described later. When a saccade signal is detected (Yes in S1003), the saccade detection unit 104 outputs a saccade detection signal to the calibration index presenting unit 103. In a similar way, the saccade detection unit 104 outputs the saccade detection signal and the electro-oculogram change amount $V_{a-b}$ to the calibration parameter calculating unit 105.

Next, the calibration index presenting unit 103 which has received the saccade detection signal determines whether or not all calibration indexes have been presented to the user (S1004). The number of calibration indexes to be presented may be specified in advance, or whether or not to continue presenting the calibration indexes may be asked to the user. It is to be noted that, the number of the calibration indexes to be presented is assumed to be two in the description of the Embodiment 1.

At this point, only the first calibration index 20 is presented (No in S1004), and thus the calibration index presenting unit 103 presents the next calibration index (S1002). More specifically, the first calibration index 20 is deleted from the display 10 and the second calibration index 30 is displayed on the display 10. Further, the calibration index presenting unit 103 notifies the calibration parameter calculating unit 105 of the position information of the second calibration index 30.

Next, the saccade detection unit 104 monitors the electro-oculogram original signal to see whether or not a saccade signal is included (S1003). When the second calibration index 30 is displayed on the display 10, the gaze-path of the user moves from the first calibration index 20 to the second calibration index 30. At this time, a saccade signal appears.

The saccade detection unit 104 which has detected the saccade signal outputs the saccade detection signal and the electro-oculogram change amount $V_{a-b}$ in the same manner as the previous time. Further, after the second calibration index 30 is presented, the calibration index presenting unit 103, in the Step S1004, determines that all of the calibration indexes have been presented (Yes in S1004).

Next, the calibration parameter calculating unit 105 calculates a new calibration parameter based on the position information of the first and the second calibration indexes 20 and 30 received from the calibration index presenting unit 103 and the electro-oculogram change amount $V_{a-b}$ after the output of the second calibration index 30, which has been received from the saccade detection unit 104 (S1005). More specifically, an eyeball movement angle θ is calculated using the position information of the first and the second calibration indexes 20 and 30. Then, the electro-oculogram change amount $V_{a-b}$ and the eyeball movement angle θ are substituted into the expression 1 to obtain a calibration coefficient α.

It is to be noted that, the method of calculating the calibration coefficient α is described as an example of updating a calibration parameter. However, the method of updating the calibration parameter is not limited to this. For example, it is also possible to use the electro-oculogram change amount, the eyeball movement angle, or the calibration index position which have been input to the calibration parameter calculating unit 105 to update a table holding plural combinations of the electro-oculogram change amount and a corresponding eyeball movement angle or a gaze-path position as shown in FIG. 2S and FIG. 2B. In this case, the number of records of the tables in FIG. 2A and FIG. 2B increases by increasing the total number of the calibration indexes to be presented, and thus it is possible to obtain a more reliable calibration parameter.

According to the structure of the Embodiment 1 as described above, the saccade signal is detected from the electro-oculogram original signal and the calibration parameter is updated by using the amount of change in the electro-oculogram which occurred during saccadic movement. As a result, it is possible to properly calculate the calibration parameter without being affected by a drift which is the problem of conventional methods.

Further, it is possible to update a calibration parameter while inducing a saccade of a user. As a result, the user only has to follow a calibration index with his eyes, and thus it is possible to reduce the burden of the user at the time of calibration.

Further, it is also possible to reduce a calibrate time by holding the calibration parameter as a table as shown in FIG. 2A and FIG. 2B.

Further, it is possible to reduce a memory by holding the calibration parameter as a slope of function (calibration coefficient α) of the electro-oculogram change amount $V_{a-b}$ and the eyeball movement angle θ.

Next, the method of detecting the saccade signal in the electro-oculogram original signal in the saccade detection unit 104 will be described in detail. It is to be noted that, a saccade signal is widely used for detecting a state of eye movement of a user not only in the eye gaze tracking apparatus 100 described above but also in the area such as medical equipment, driver supporting devices, user interfaces, and the like. Therefore, it is significantly effective to detect a saccade signal with ease and high accuracy.

For example, the method of detecting a saccade signal from an electro-oculogram original signal includes techniques disclosed by the following Patent Literatures 3 to 5.

Japanese Unexamined Patent Application Publication No 11-276461 (Patent Literature 3) discloses a technique of detecting a saccade signal of an operator and determines attentiveness of the operator base on an occurrence frequency. It is to be noted that, a high pass filter having a cutoff frequency of 0.05 to 0.1 Hz is used for detecting a saccade signal.

Japanese Unexamined Patent Application Publication No 9-034631 (Patent Literature 4) discloses a technique for eliminating the need for manually positioning a pointer on the display screen and a gaze-point of an operator. More specifically, when a saccade signal is detected within a predetermined period of time after a symbol for calibration is generated on the display screen, it is determined that the symbol for calibration and the gaze-point of the operator have matched, and then the position of the pointer is calibrated. It is to be noted that, a high pass filter having a cutoff frequency of 0.05 to 0.1 Hz is used for detecting a saccade signal.

Japanese Unexamined Patent Application Publication No 2002-272693 (Patent Literature 5) discloses a technique for detecting an end point of a saccadic movement on the basis of an eye-movement signal. Then, each time a saccadic movement ends, brain waves within a predetermined period of time from the end point is consecutively stored for plural parts of the brain as unit brain waves, so that an eye fixation related potential is obtained. It is to be noted that, a saccade signal is detected by determining whether or not the direction of an eye movement has changed after continuously stayed the same within a predetermined period of time.

Figure 7:
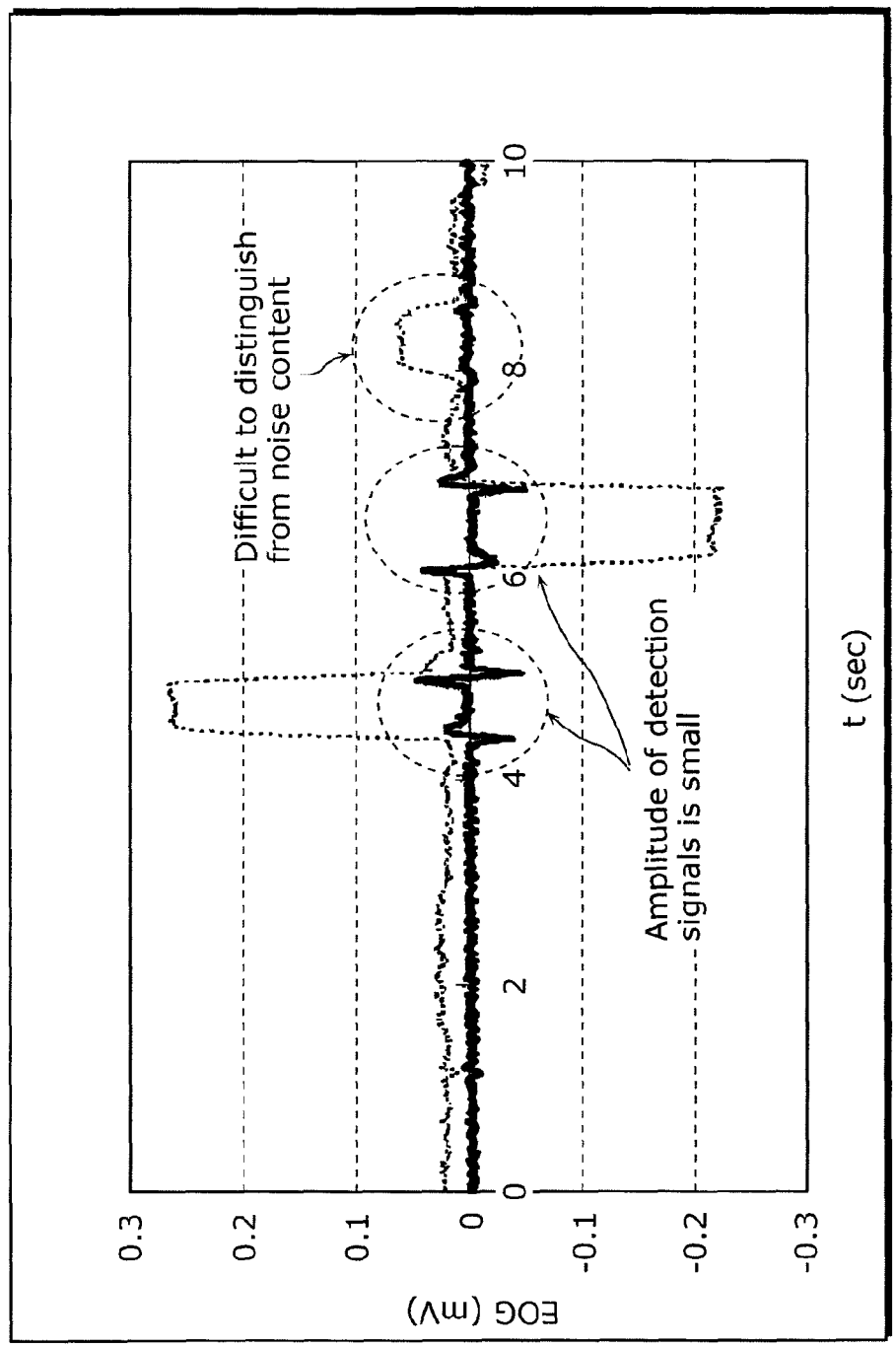
FIG. 7 is a diagram that shows an electro-oculogram signal obtained by applying a high pass filter processing on the electro-oculogram signal of FIG. 3.

The methods of detecting a saccade as disclosed in Patent Literatures 3 to 5 may be adopted for the saccade detection unit 104 shown in FIG. 1. However, with the methods as shown in the Patent Literatures 3 and 4, a saccade signal is detected by using a high pass filter. When the electro-oculogram original signal shown in FIG. 3 passes a high pass filter, amplitude of a saccade signal can be small in some cases as shown in FIG. 7. It can be difficult especially for a saccade signal with small amplitude to be distinguished from noise component.

Further, with the method shown in the Patent Literature 5, there is a possibility of false detection such as the case in which, when detecting the direction of eye movement, the direction of eye movement is not determined as continuously the same even during a saccade due to an effect of noise component or the like.

Thus, in the Embodiments 2 to 5 according to the present invention, a method of detecting a saccade signal from an electro-oculogram original signal of a user with ease and high accuracy will be described.

Embodiment 2

Figure 8:
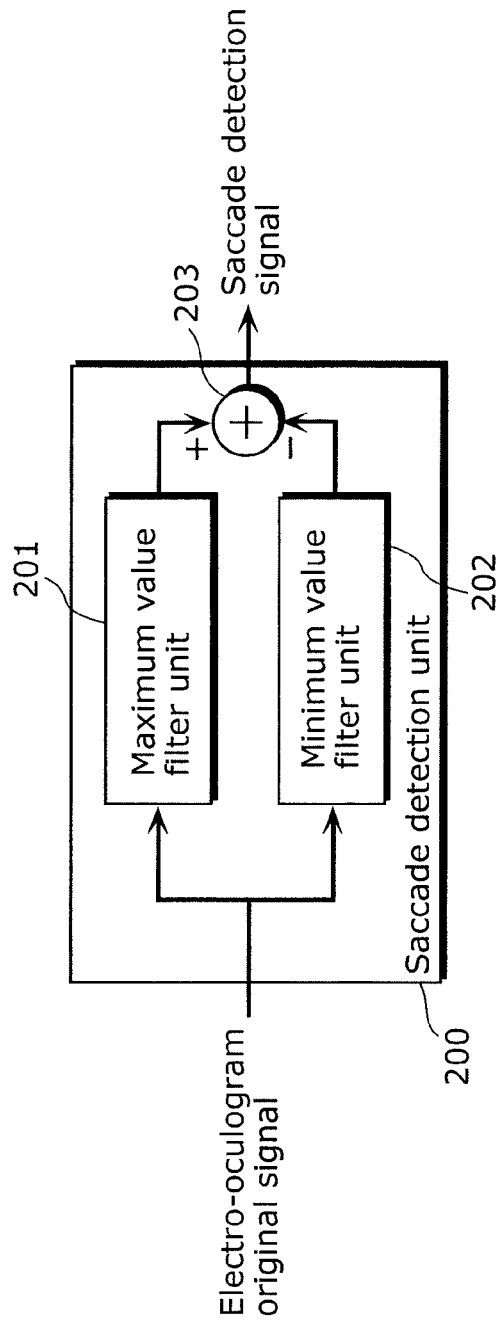
FIG. 8 is a block diagram of a saccade detection unit according to Embodiment 2.

FIG. 8 is a block diagram that shows a structure of a saccade detection unit 200 according to Embodiment 2 of the present invention. The saccade detection unit 200 shown in FIG. 8 includes: a maximum value filter unit (the first filtering unit) 201 which performs maximum value filtering on an electro-oculogram original signal; a minimum value filter unit (the second filtering unit) 202 which performs minimum value filtering on the electro-oculogram original signal; and a subtraction unit 203.

More specifically, the maximum value filter unit 201 and the minimum value filter unit 202 are connected in parallel to each other. The maximum value filter unit 201 performs the maximum value filtering on the electro-oculogram original signal and outputs the first electro-oculogram signal. The minimum value filter unit 202 performs the minimum value filtering on the electro-oculogram original signal and outputs the second electro-oculogram signal. Then, the subtraction unit 203 subtracts the second electro-oculogram signal from the first electro-oculogram signal to generate an output signal.

It is to be noted that, the present invention is intended for the case where a blink component of a user is not included in the electro-oculogram original signal, such as the case where electrodes are placed on the right and left of an eyeball as shown in FIGS. 36A and 36B, or the measuring method where electrodes are placed at a position away from the eye. Descriptions will be given as to detection of a saccade signal when such a measuring method is used.

Next, processing of the maximum value filter unit 201 as shown in FIG. 8 will be described. The maximum value filter unit 201 performs filtering process described below on the electro-oculogram original signal f (x).

$$f\max(x) = \max(f\max(x), f(x+i))$$

When n is an odd number, the following applies. $(-n/2 < i < n/2)$

When n is an even number, one of the followings applies. $(-n/2 \leq i < n/2)$ or $(-n/2 < i \leq n/2)$ Here, f max (x) is an electro-oculogram signal after the maximum value filtering is performed, n is the number of filter taps, and i is an integer. Further, max (a, b) is a function that returns the value that is larger between a and b. Thus, in the maximum value filtering, a sampling value is output which has the largest amplitude in n samples centering on an arbitrary sample f (x) among the electro-oculogram original signals. The first electro-oculogram signal can be obtained by performing the above processing on each of the samples of the electro-oculogram original signals.

Figure 9:
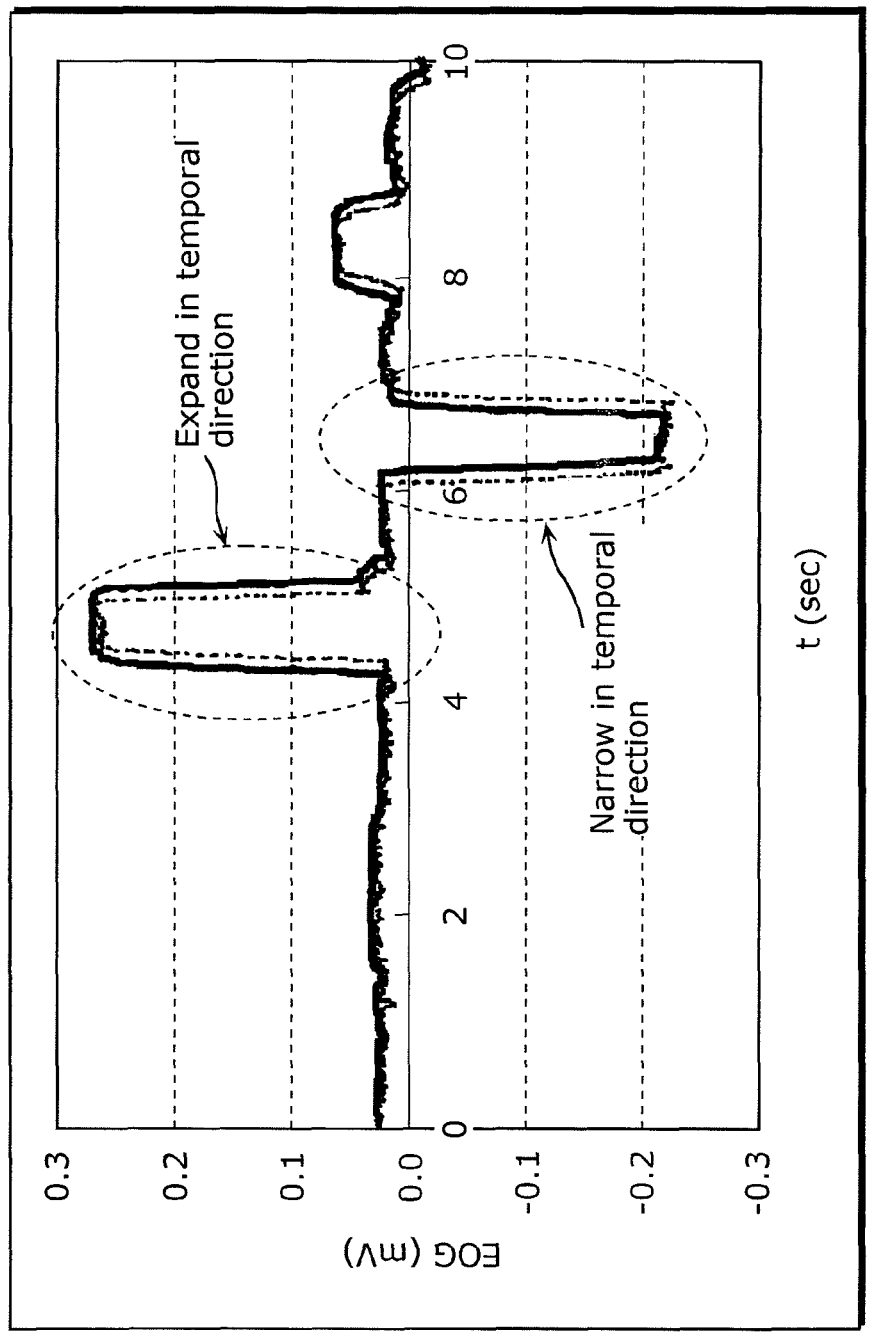
FIG. 9 is a diagram that shows an electro-oculogram signal obtained by applying a maximum value filtering (unit processing period=0.25 seconds) on the electro-oculogram signal of FIG. 3.

FIG. 9 shows an example of performing the above-described filtering processing on the electro-oculogram original signal of FIG. 3. It is to be noted that the unit processing period for the maximum value filtering is set to 0.25 seconds for detecting the saccade signal from the electro-oculogram original signal. It is to be noted that, the unit processing period indicates a time interval including a sample on which a single maximum value filtering is performed. Further, the number of filter taps n of the maximum value filtering unit 201 is the number of samples included in the unit processing period (0.25 seconds). Thus, the number of filter taps n can be calculated using the unit processing period and a sampling frequency when A/D conversion is performed on the electro-oculogram original signal.

Figure 10:
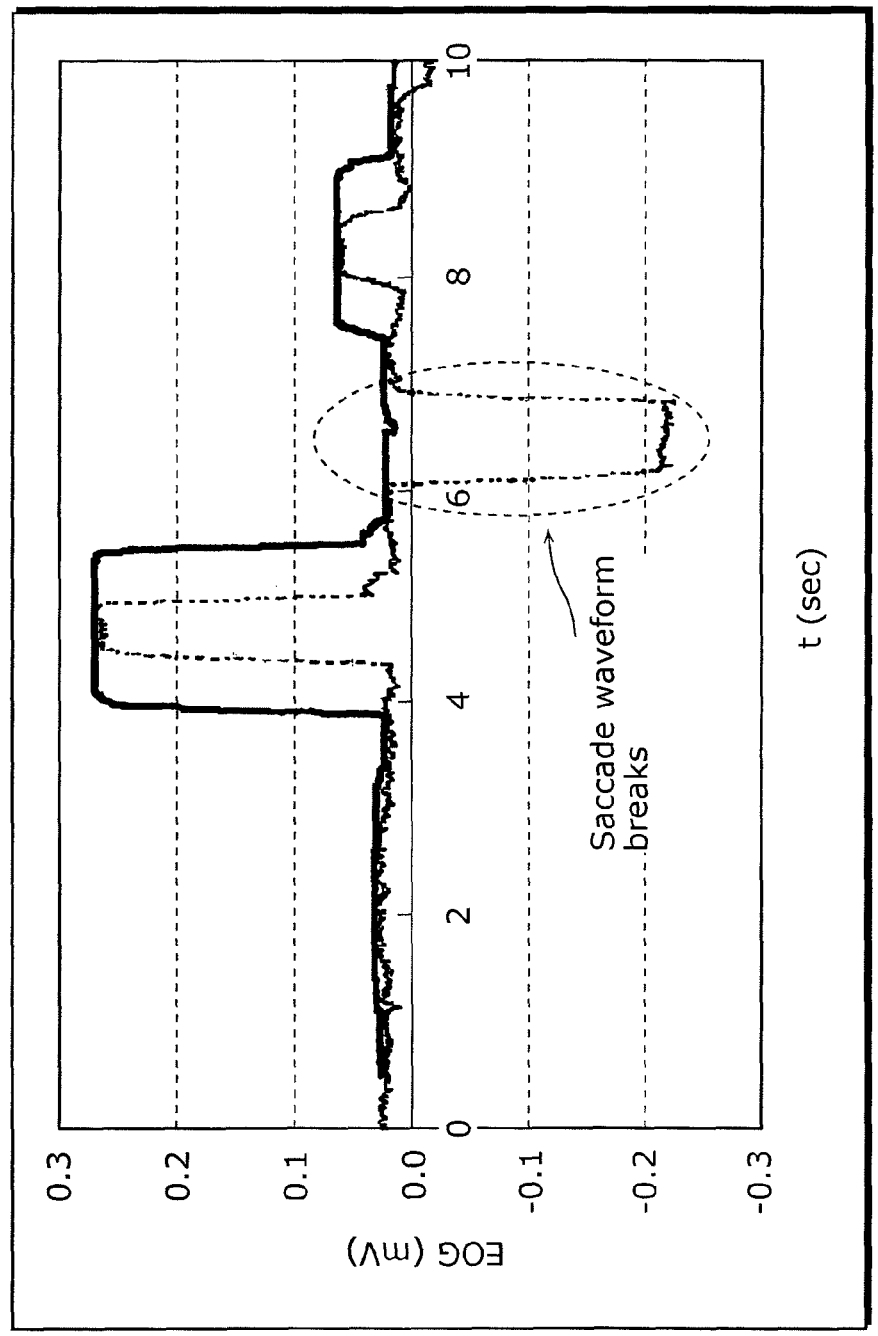
FIG. 10 is a diagram that shows an electro-oculogram signal obtained by applying a maximum value filtering (unit processing period=1.0 second) on the electro-oculogram signal of FIG. 3.

As shown in FIG. 9, when the maximum value filtering is performed on the electro-oculogram original signal, a plus signal expands in the temporal direction and a minus signal narrows in the temporal direction. However, when the unit processing period of the maximum value filter unit 201 becomes larger than a general fixation time (0.3 to 0.4 seconds, approximately), the saccade waveform in the minus direction breaks as shown in FIG. 10. FIG. 10 is an example of performing the maximum value filtering with the unit processing period being 1.0 second. Since the saccade signal cannot be detected when the saccade waveform breaks as shown in FIG. 10, it is necessary to set the unit processing period of the maximum value filter unit 201 to be shorter than the general fixation time.

It is to be noted that, although an example in which the unit processing period of the maximum value filtering is 0.25 seconds has been described in the Embodiment 2, the unit processing period may be any value as long as it is shorter than the general fixation time.

Next, a processing of the minimum value filter unit 202 will be described. The minimum value filter unit 202 performs filtering described below on the electro-oculogram original signal f (x).

$$f\min(x) = \min(f\min(x), f(x+i))$$

When n is an odd number, the following applies. $(-n/2 < i < n/2)$

When n is an even number, one of the followings applies. $(-n/2 \leq i < n/2)$ or $(-n/2 < i \leq n/2)$ Here, f min (x) is an electro-oculogram signal after the minimum value filtering is performed, n is the number of filter taps, and i is an integer. Further, min (a, b) is a function that returns the value that is smaller between a and b. Thus, in the minimum value filtering, a sampling value is output which has the smallest amplitude in n samples centering on an arbitrary sample f (x) among the electro-oculogram original signals. The second electro-oculogram signal can be obtained by performing the above processing on each of the samples of the electro-oculogram original signals.

Figure 11:
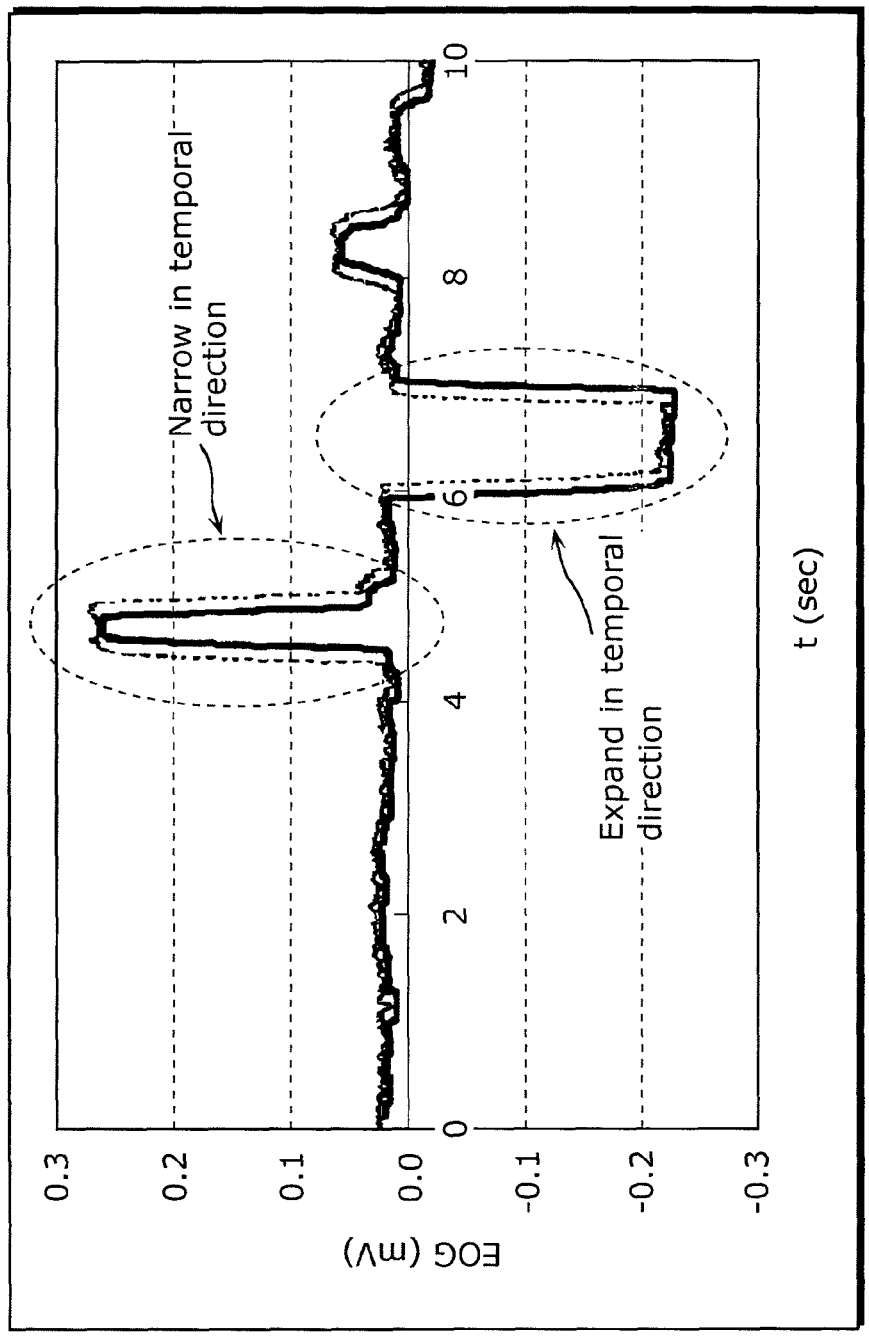
FIG. 11 is a diagram that shows an electro-oculogram signal obtained by applying a minimum value filtering (unit processing period=0.25 seconds) on the electro-oculogram signal of FIG. 3.

FIG. 11 shows an example of performing the above-described filtering processing on the electro-oculogram original signal of FIG. 3.

In FIG. 11, the unit processing period for the minimum value filtering is set to 0.25 seconds for detecting the saccade signal from the electro-oculogram original signal.

Figure 12:
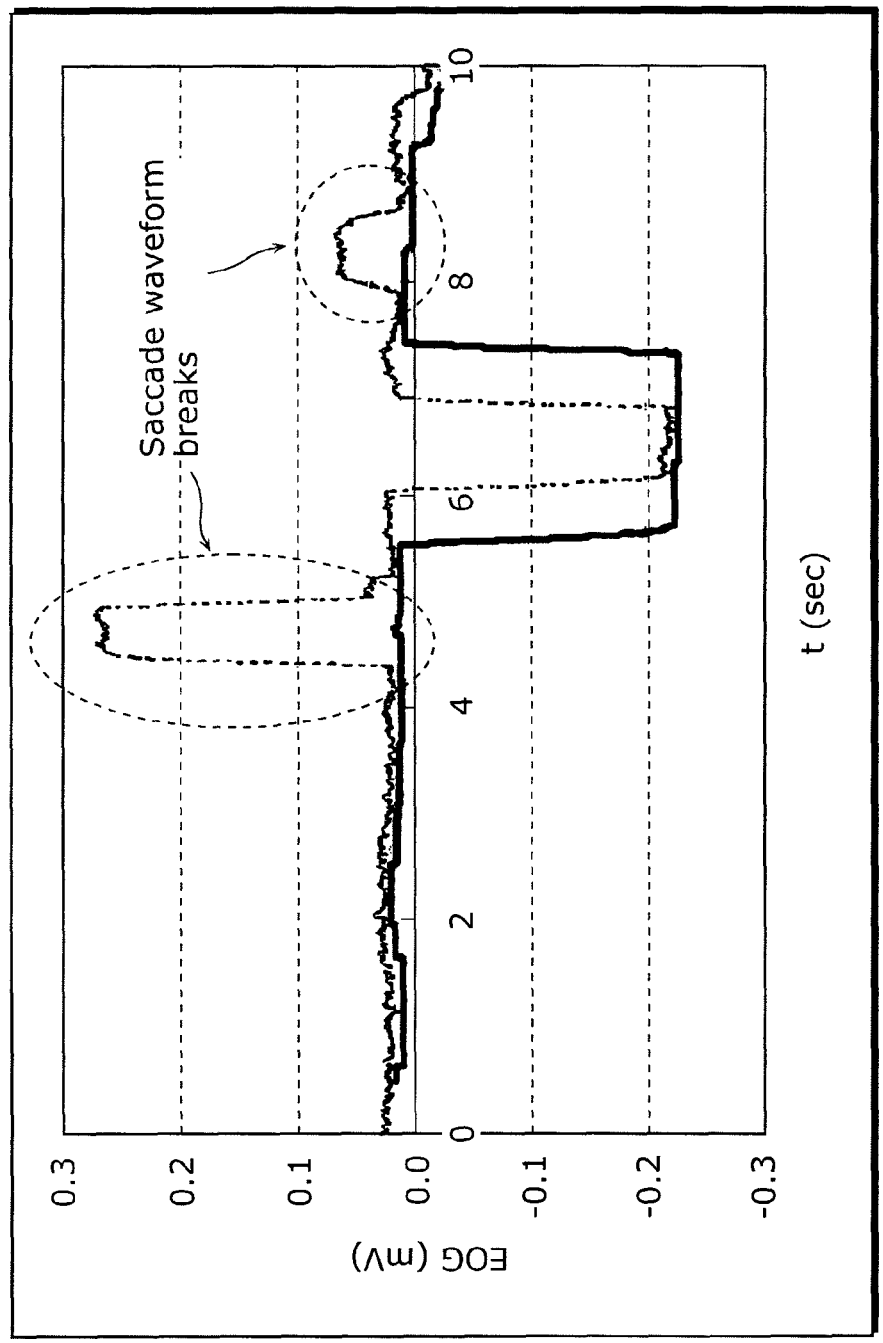
FIG. 12 is a diagram that shows an electro-oculogram signal obtained by applying a minimum value filtering (unit processing period=1.0 second) on the electro-oculogram signal of FIG. 3.

As shown in FIG. 11, when the minimum value filtering is performed on the electro-oculogram original signal, a plus signal narrows in the temporal direction and a minus signal expands in the temporal direction. Here, when the unit processing period of the minimum value filter unit 202 becomes larger than a general single fixation time, the saccade waveform in the plus direction breaks as shown in FIG. 12. FIG. 12 is an example of performing the minimum value filtering with the unit processing period being 1.0 second. Since a saccade component cannot be detected when the saccade waveform breaks as shown in FIG. 12, it is necessary to set the unit processing period of the minimum value filter unit 202 to be shorter than the general fixation time.

It is to be noted that, although an example in which the unit processing period of the minimum value filter unit is 0.25 seconds has been described in the Embodiment 2, the unit processing period may be any value as long as it is shorter than the general fixation time.

Next, the processing of the subtraction unit 203 will be described. The subtraction unit 203 subtracts the second electro-oculogram signal f min (x) which has been output from the minimum value filter unit 202, from the first electro-oculogram signal f max (x) which has been output from the maximum value filter unit 201, thereby extracting the saccade signal.

FIG. 4 shows a signal indicating a difference between the first electro-oculogram signal shown in FIG. 9 and the second electro-oculogram signal shown in FIG. 11. It can be understood by referring to FIG. 4 that the detection signal including the period of time when a saccade has occurred is obtained.

The saccade detection unit 200 generates a saccade detection signal and an electro-oculogram change amount based on an output signal as shown in FIG. 4 to output to the calibration index presenting unit 103 and the calibration parameter calculating unit 105. For example, when the amount of change in sampling values within a period of time corresponding to a period of time required for saccadic movement exceeds a predetermined threshold, it is determined that a saccadic movement has occurred and a saccade detection signal is output. Further, the amount of change in sampling values is output as an electro-oculogram change amount.

It is to be noted that, although the maximum value filter unit 201 and the minimum value filter unit 202 are used in the Embodiment 2, a filter that selects a value close to the maximum value or the minimum value may be used. In this case, it is desirable to select a value approximately 90% of the maximum value or the minimum value.

Further, although the Embodiment 2 has shown an example in which the unit processing period (the number of filter taps) of the maximum value filter unit 201 and the minimum value filter unit 201 are set to the same value, difference values may be set.

According to the structure of the Embodiment 2 as described above, a saccade signal is detected by performing each of the maximum value filtering and the minimum value filtering on the electro-oculogram original signal and subtracting the second electro-oculogram signal on which the minimum value filtering has been performed, from the first electro-oculogram signal on which the maximum value filtering has been performed. As a result, it is possible to easily obtain a saccade signal that includes the time when a saccade occurred.

Embodiment 3

Figure 13:
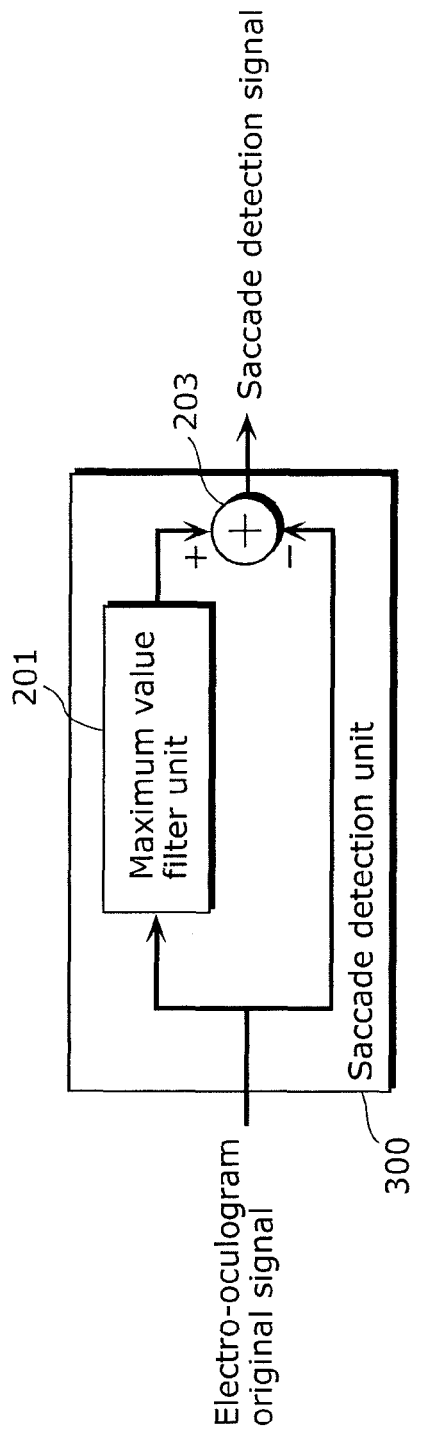
FIG. 13 is a block diagram of a saccade detection unit according to Embodiment 3.

FIG. 13 is a block diagram that shows a structure of a saccade detection unit 300 according to Embodiment 3 of the present invention.

The saccade detection unit 300 according to the Embodiment 3 includes the maximum value filtering unit (the first filtering unit) 201 and the subtraction unit 203. More specifically, it is different from the Embodiment 2 in that the minimum value filter unit 202 is omitted. By omitting the minimum value filter unit 202, it is possible to easily obtain a saccade signal while reducing the amount of processing.

In FIG. 13, since the structure same as the structure in FIG. 8 has already been described, the same numerals are assigned and the description that is overlapped will be omitted. In the saccade detection unit 300 according to the Embodiment 3, an electro-oculogram original signal enters two paths. Then, one passes the maximum value filter unit 201 to be input into the subtraction unit 203 as the first electro-oculogram signal and the other is directly input into the subtraction unit 203 as the second electro-oculogram signal. Then, the subtraction unit 203 subtracts the electro-oculogram original signal f (x) (corresponding to "the second electro-oculogram signal") from the first electro-oculogram signal f max (x) on which the maximum value filtering has been performed to output the saccade signal, which differs from the Embodiment 2.

Figure 14:
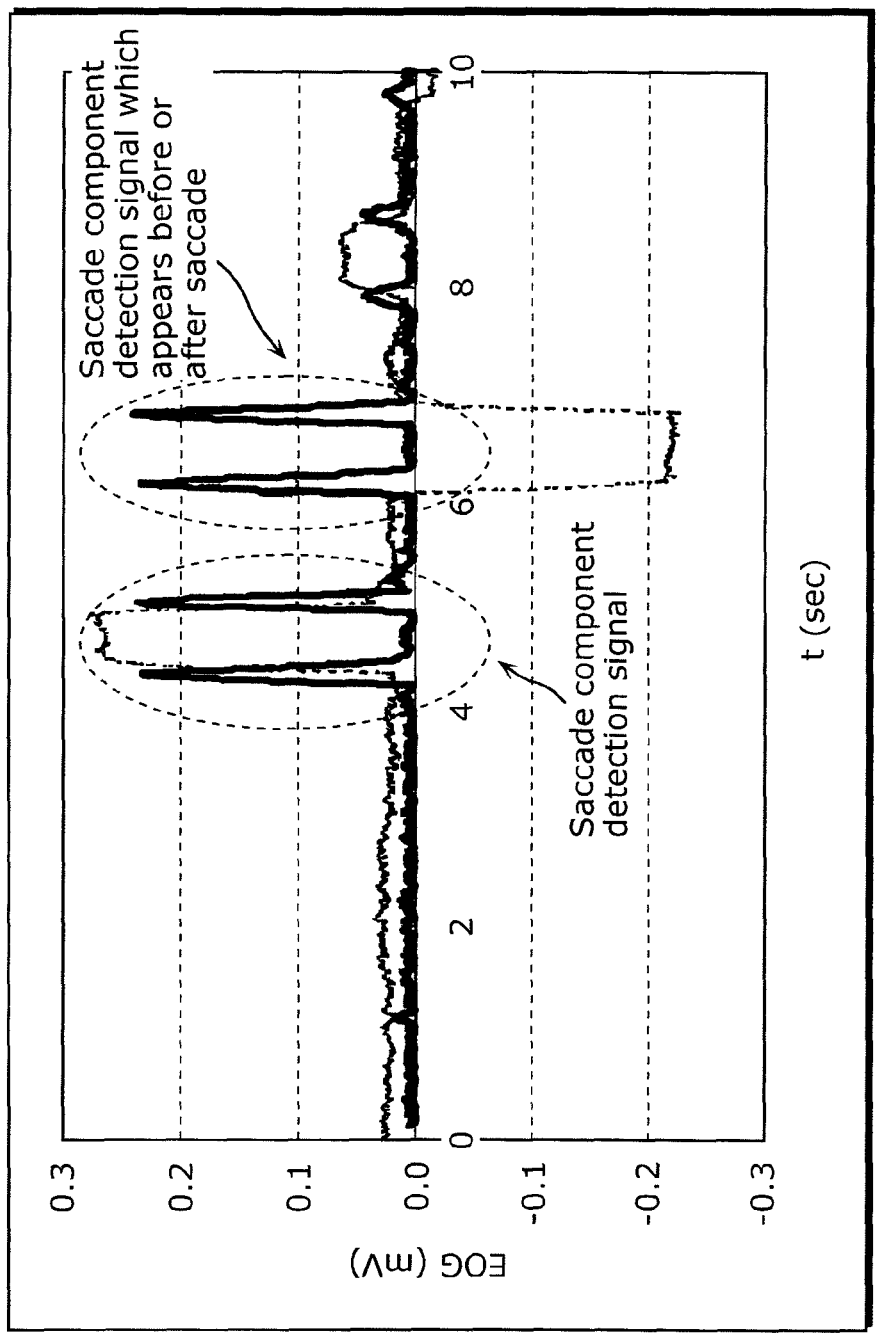
FIG. 14 is a diagram that shows a saccade detection signal obtained by subtracting the electro-oculogram signal of FIG. 3 from the electro-oculogram signal of FIG. 9.

FIG. 14 shows a signal indicating a difference between the first electro-oculogram signal on which the maximum value filtering has been performed as shown in FIG. 9 and electro-oculogram original signal shown in FIG. 3. It can be understood by referring to FIG. 14 that the detection signal is obtained when a saccade occurs.

The saccade detection unit 300 generates a saccade detection signal and an electro-oculogram change amount based on an output signal as shown in FIG. 14 to output to the calibration index presenting unit 103 and the calibration parameter calculating unit 105. For example, when the amount of change in sampling values within a period of time corresponding to a period of time required for saccadic movement exceeds a predetermined threshold, it is determined that a saccadic movement has occurred and a saccade detection signal is output. Further, the amount of change in sampling values is output as an electro-oculogram change amount.

The detection signal of the saccade component in the minus direction, however, appears before or after the time when a saccade occurs. Thus, the Embodiment 3 is effective in terms of a processing amount when obtaining an occurrence frequency and the like of a saccade, which does not require temporal information.

It is to be noted that, although the maximum value filter unit 201 is used in the Embodiment 3, a filter that selects a value close to the maximum value may be used. In this case, it is desirable to select a value approximately 90% of the maximum value.

According to the structure of the Embodiment 3 as described above, it is possible to obtain a saccade signal easily because the saccade signal is detected by subtracting an electro-oculogram original signal from the first electro-oculogram signal obtained by performing the maximum value filtering on the electro-oculogram original signal.

Embodiment 4

Figure 15:
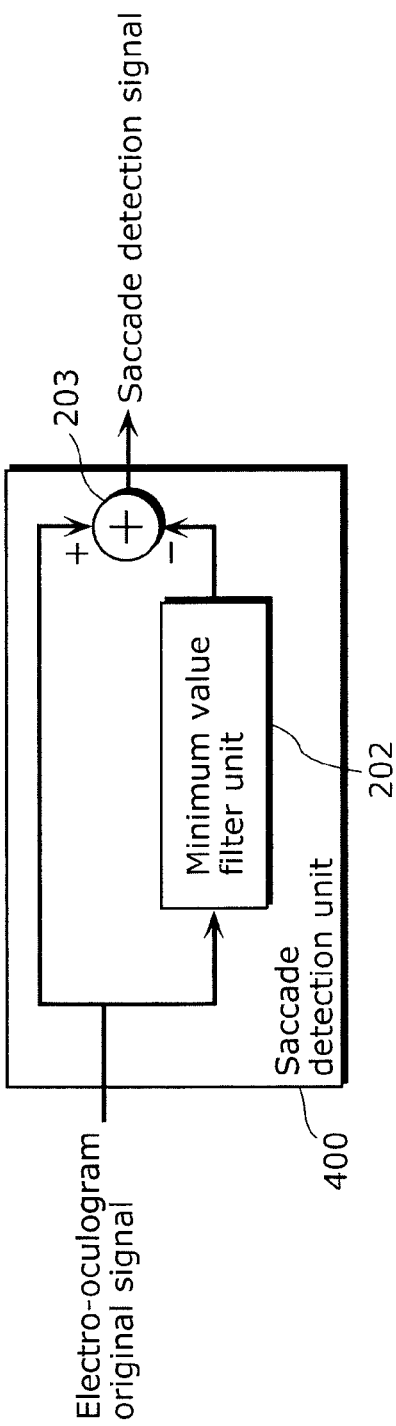
FIG. 15 is a block diagram of a saccade detection unit according to Embodiment 4.

FIG. 15 is a block diagram that shows a structure of a saccade detection unit 400 according to Embodiment 4 of the present invention.

The saccade detection unit 400 according to the Embodiment 4 includes the minimum value filter unit (the first filtering unit) 202 and the subtraction unit 203. More specifically, it is different from the Embodiment 2 in that the maximum value filter unit 201 is omitted. By omitting the maximum value filter unit 201, it is possible to easily obtain a saccade signal while reducing the amount of processing.

In FIG. 15, since the structure same as the structure in FIG. 8 has already been described, the same numerals are assigned and the description that is overlapped will be omitted. In the saccade detection unit 400 according to the Embodiment 4, an electro-oculogram original signal enters two paths. Then, one passes the minimum value filter unit 202 to be input into the subtraction unit 203 as the first electro-oculogram signal and the other is directly input into the subtraction unit 203 as the second electro-oculogram signal. Then, the subtraction unit 203 subtracts the first electro-oculogram signal f min (x) on which the minimum value filtering has been performed, from the electro-oculogram original signal f (x) (corresponding to "the second electro-oculogram signal") to output the saccade signal, which differs from the Embodiment 2.

Figure 16:
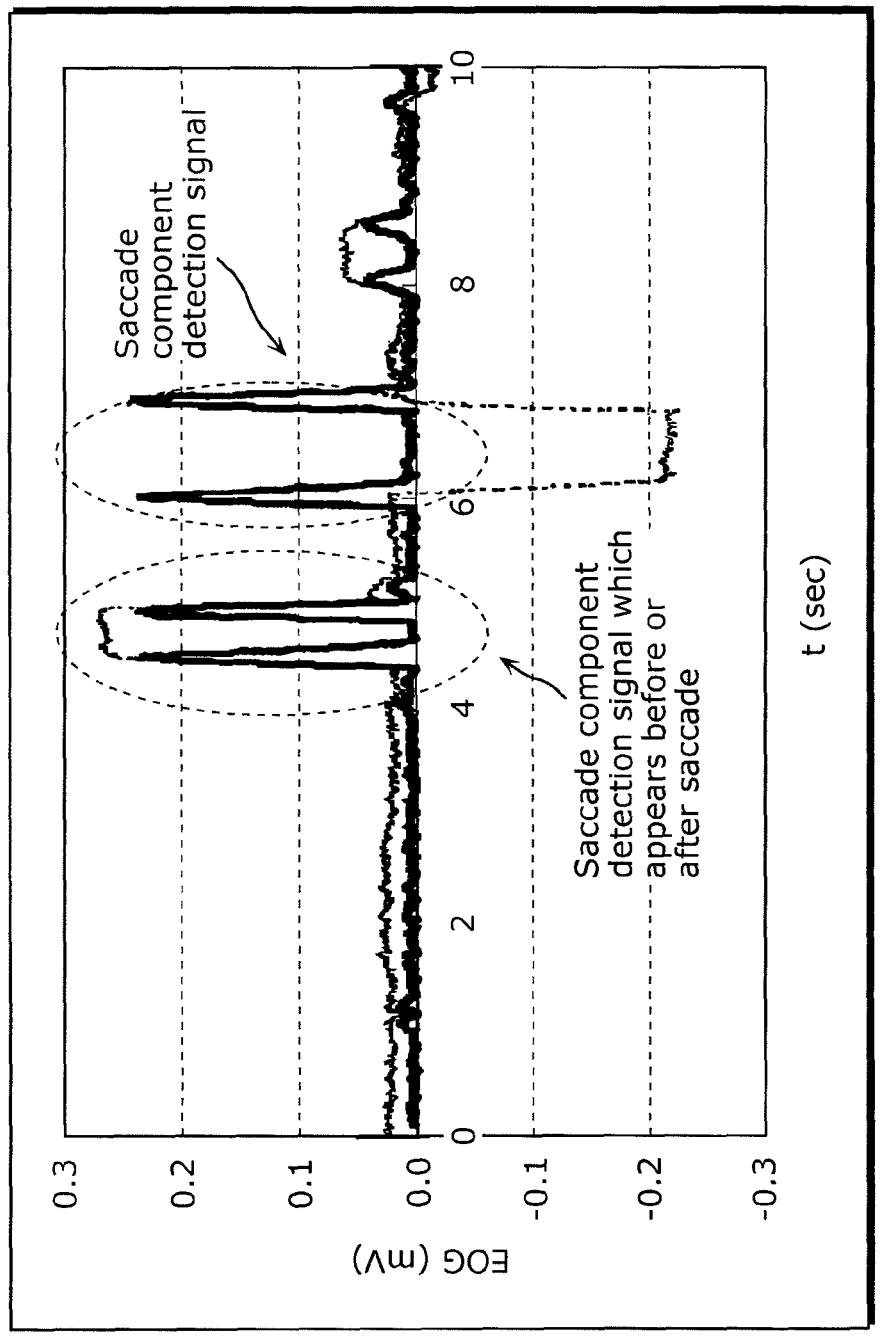
FIG. 16 is a diagram that shows a saccade detection signal obtained by subtracting the electro-oculogram signal of FIG. 11 from the electro-oculogram signal of FIG. 3.

FIG. 16 shows a signal indicating a difference between the electro-oculogram original signal shown in FIG. 3 and the second electro-oculogram signal on which the minimum value filtering has been performed as shown in FIG. 11. It can be understood by referring to FIG. 16 that the detection signal is obtained when a saccade occurs.

The saccade detection unit 400 generates a saccade detection signal and an electro-oculogram change amount based on an output signal as shown in FIG. 16 to output to the calibration index presenting unit 103 and the calibration parameter calculating unit 105. For example, when the amount of change in sampling values within a period of time corresponding to a period of time required for a saccadic movement exceeds a predetermined threshold, it is determined that a saccadic movement has occurred and a saccade detection signal is output. Further, the amount of change in sampling values is output as an electro-oculogram change amount.

The saccade signal in the plus direction, however, appears before or after the time when a saccade occurs. Thus, the Embodiment 4 is effective in terms of a processing amount when obtaining an occurrence frequency and the like of a saccade, which does not require temporal information.

It is to be noted that, although the minimum value filter unit 202 is used in the Embodiment 4, a filter that selects a value close to the maximum value may be used. In this case, it is desirable to select a value approximately 90% of the minimum value.

According to the structure of the Embodiment 4 as described above, it is possible to obtain a saccade signal easily because the saccade signal is detected by subtracting, from the electro-oculogram original signal (the second electro-oculogram), the first electro-oculogram signal obtained by performing the minimum value filtering on the electro-oculogram original signal.

Embodiment 5

Figure 17:
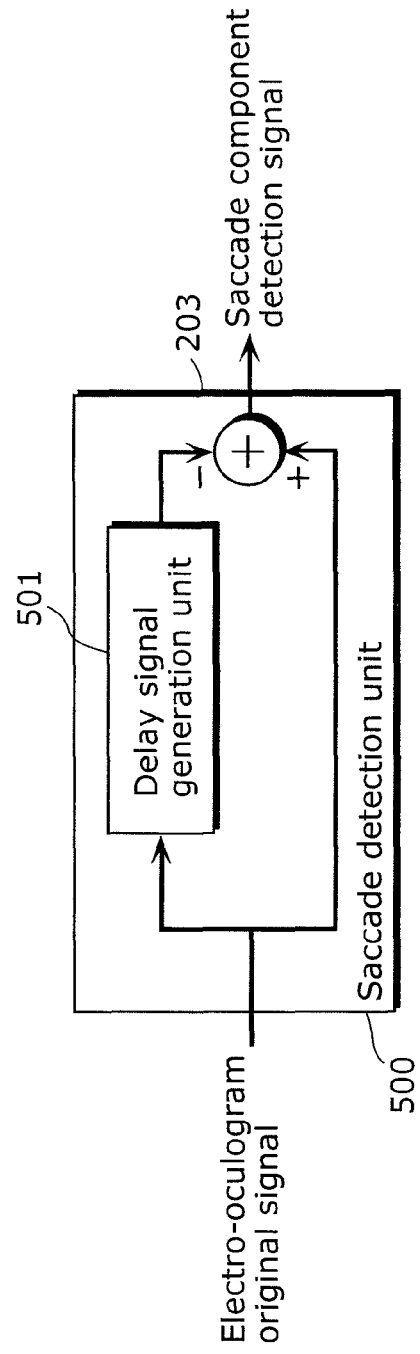
FIG. 17 is a block diagram of a saccade detection unit according to Embodiment 5.

Next, a block diagram of a saccade detection unit 500 according to Embodiment 5 will be shown in FIG. 17.

The saccade detection unit 500 according to Embodiment 5 includes a delay signal generation unit 501 and the subtraction unit 203. The delay signal generation unit 501 delays an electro-oculogram original signal for a predetermined amount of time and outputs a delay signal. Further, an electro-oculogram original signal input into the saccade detection unit 500 enters two paths. Then, one passes the delay signal generation unit 501 to be input into the subtraction unit 203 as the delay signal and the other is directly input into the subtraction unit 203. Then, the subtraction unit 203 subtracts the delay signal from the electro-oculogram original signal to output a saccade signal. It is possible to easily obtain a singed saccade signal by including the delay signal generation unit 501.

Processing of the delay signal generation unit 501 as shown in FIG. 17 will be described. The delay signal generation unit 501 performs the following processing on an electro-oculogram original signal f (x).

$$f \text{delay}(x) = f(x-t)$$

Figure 18:
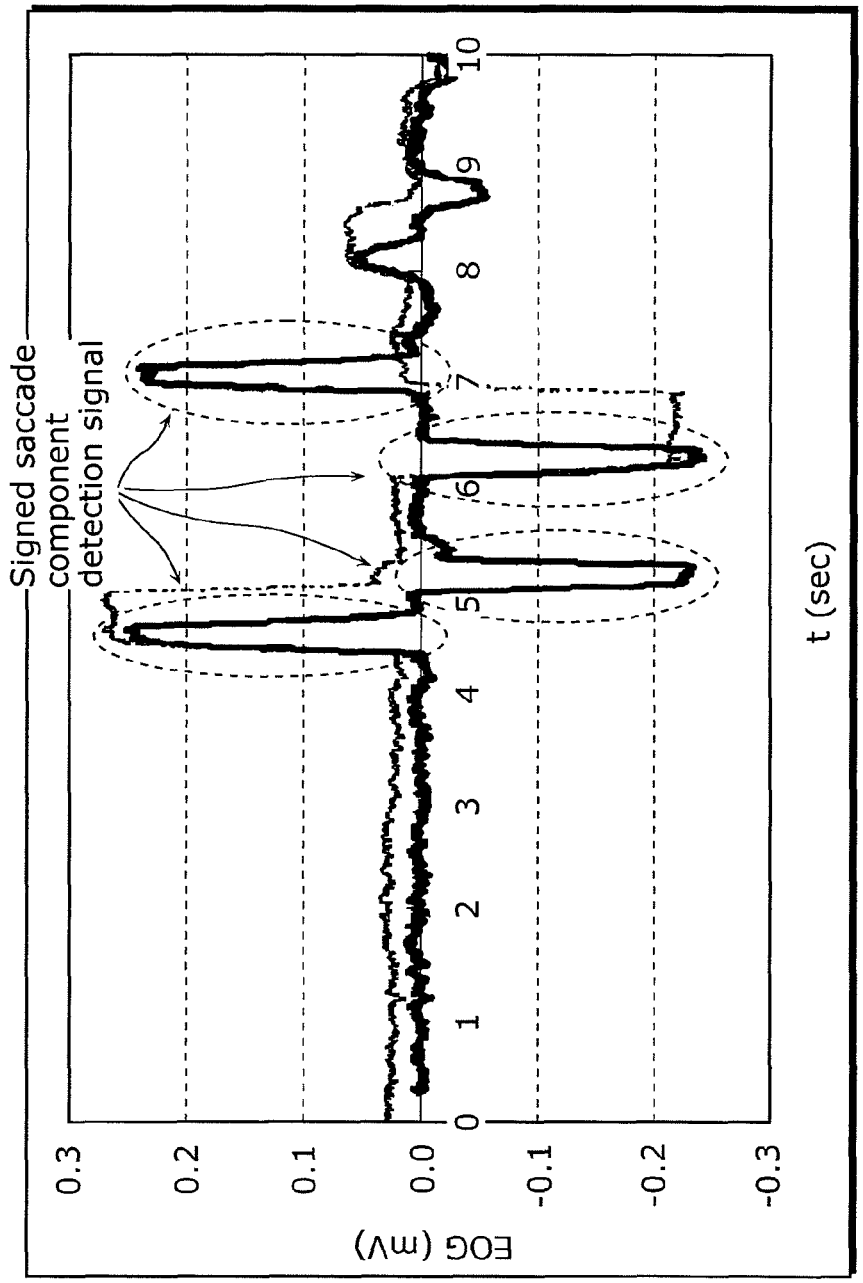
FIG. 18 is a diagram that shows a saccade detection signal when a delay time of a delay signal generation unit is 0.25 seconds.

Here, f delay (x) is an electro-oculogram signal after delay processing, and t is a delay time. The delay signal can be obtained by performing the delay processing described above on the electro-oculogram original signal shown in FIG. 3. Then, FIG. 18 shows an example where the delay signal is subtracted from the electro-oculogram original signal by the subtraction unit 203. It is to be noted that, in order to detect a signed saccade component, the delay time is specified as t=0.25 seconds. It can be understood by referring to FIG. 18 that the singed saccade signal including the period of time when the saccade occurs is obtained.

The saccade detection unit 500 generates a saccade detection signal and an electro-oculogram change amount based on an output signal as shown in FIG. 18 to output to the calibration index presenting unit 103 and the calibration parameter calculating unit 105. For example, when the amount of change in sampling values within a period of time corresponding to a period of time required for a saccadic movement exceeds a predetermined threshold, it is determined that a saccadic movement has occurred and a saccade detection signal is output. Further, the amount of change in sampling values is output as an electro-oculogram change amount.

Figure 19:
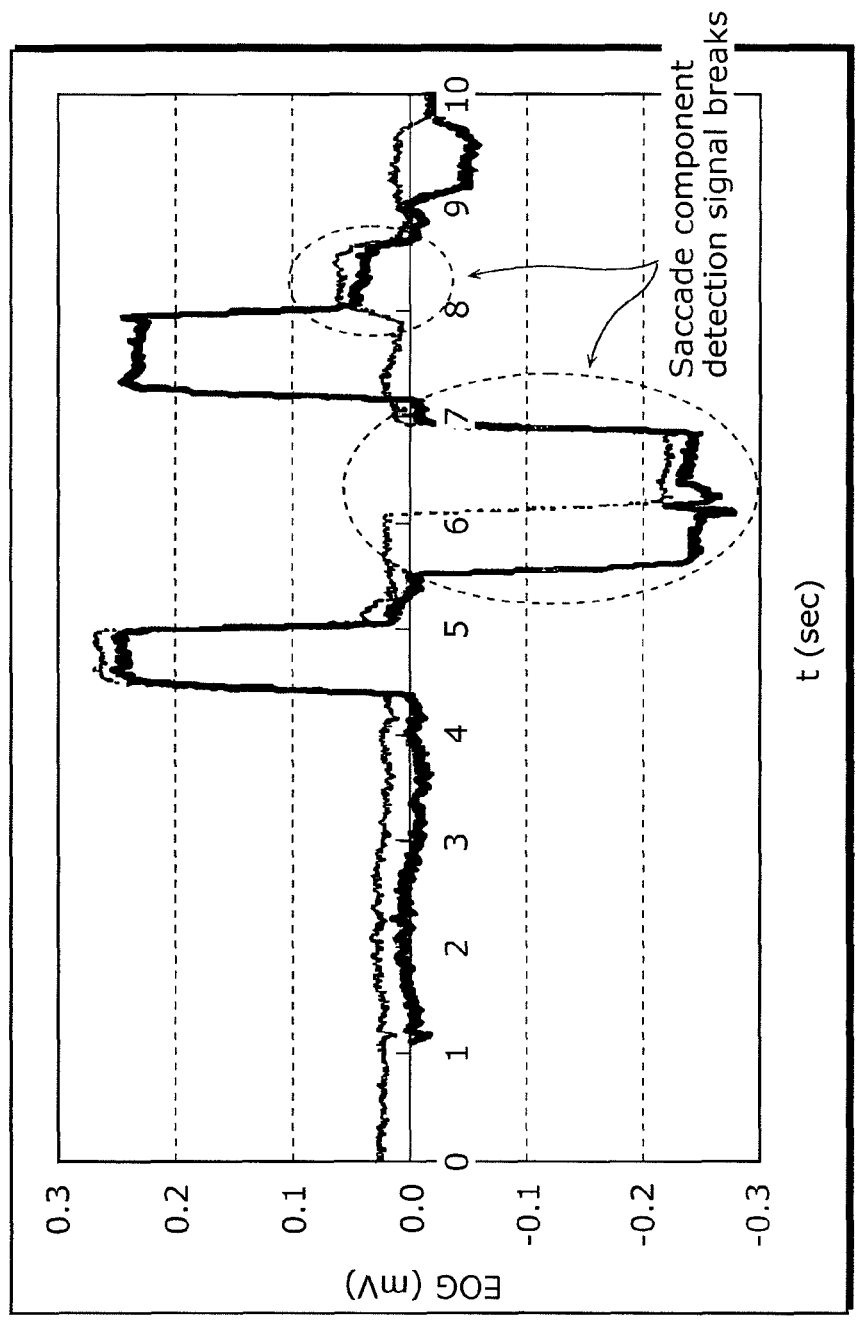
FIG. 19 is a diagram that shows a saccade detection signal when a delay time of a delay signal generation unit is 1.1 seconds.

Here, when the delay time t becomes larger than a general single fixation time=(from 0.3 to 0.4 seconds, approximately), the saccade signal breaks as shown in FIG. 19. FIG. 19 is an example where the delay time t is 1.1 seconds. When the saccade signal breaks as shown in FIG. 19, the saccade signal cannot be extracted. Thus, the delay time t of the delay signal generation unit 501 needs to be shorter than the general single fixation time. It is to be noted that, although the delay time of 0.25 seconds is applied as an example in the Embodiment 5, any value can be applied as long as the delay time is shorter than the general single fixation time.

According to the structure of the Embodiment 5 as described above, a signed saccade signal is detected by generating a delay signal from an electro-oculogram original signal and subtracting the delay signal from the electro-oculogram original signal. Thus, it is effective in that saccade signals can be distinguished between plus and minus.

Next, a method of measuring an electro-oculogram in consideration of an effect of a blink will be described. When detecting an eye movement by utilizing a change in an electro-oculogram as in the EOG and the like, there is a problem of an effect of a signal generated by a blink of a user (hereinafter referred to as "blink signal").

In some cases, the blink signal is generated invariably in the plus direction, or invariably in the minus direction, depending on the method for measuring the electro-oculogram. FIG. 20A to FIG. 20D show examples of placement patterns of the electro-oculogram measuring unit and the method for measuring the electro-oculogram original signal.

According to the placement pattern of FIG. 20A, the electrodes A and B are placed above and below an eye, respectively, and a difference potential Va−Vb is obtained, where Va is the electro-oculogram measured by the electrode A placed above the eye and Vb is the electro-oculogram measured by the electrode B placed below the eye. In this case, the blink signal is generated invariably in the plus direction. This is because, when a human blinks, the eyeball always moves upward.

Figure 20A:
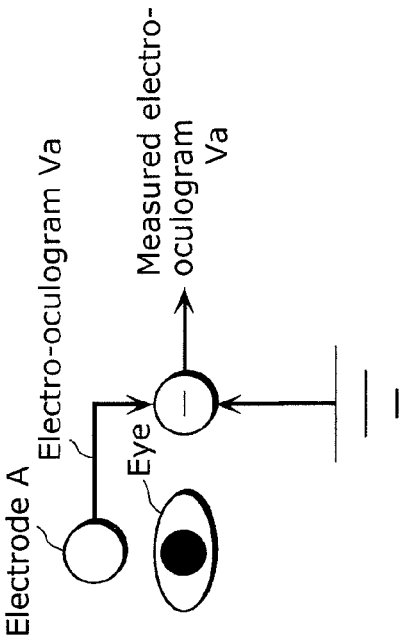
FIG. 20A is a diagram that shows an example of a pattern of attaching electrodes.
Figure 20B:
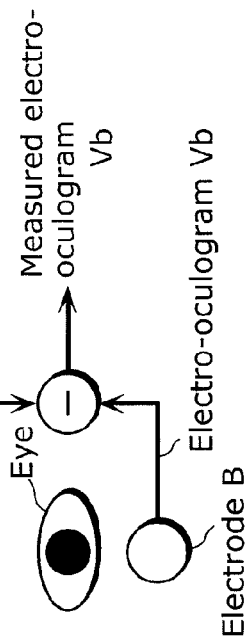
FIG. 20B is a diagram that shows another example of the pattern of attaching electrodes.

According to the placement pattern of FIG. 20B, the electrode A is placed above the eye and the other electrode is placed on the earth or a place less subject to the electro-oculogram, so that the electro-oculogram Va of the electrode A is measured. In this case also, the blink signal is generated invariably in the plus direction (at a value larger than a reference value).

Likewise, according to the placement pattern of FIG. 20C, the electrodes A and B are placed above and below the eye, respectively, and a difference potential Vb−Va is obtained, where Vb is the electro-oculogram measured by the electrode B placed below the eye and Va is the electro-oculogram measured by the electrode A placed above the eye. In this case, the blink signal is generated invariably in the minus direction. According to the placement pattern of FIG. 20D, the electrode B is placed below the eye and the other electrode is placed on the earth or a place less subject to the electro-oculogram, so that the electro-oculogram Vb of the electrode B is measured. In this case also, the blink signal is generated invariably in the minus direction.

When the user blinks during the measurement according to the placement patterns as shown in FIG. 20A and FIG. 20B, a potential is generated steeply in the plus direction (this is the "blink signal") as shown by regions (a) in FIG. 21. When the blink signal is directly used for detecting a gaze-point, the gaze-point changes rapidly and a gaze-path cannot be tracked accurately.

Here, there is a technique disclosed by Japanese Unexamined Patent Application Publication No. 11-85384 (Patent Literature 6) as a method to reduce an effect of the blink signal (a component of a signal generated by a blink) and the like from electro-oculogram original signal.

The technique disclosed by Patent Literature 6 aims to detect an electro-oculogram of a user and input a gaze-position (cursor) in real time. At this time, a delay element is introduced into a fluctuation waveform of the electro-oculogram, so that a temporal change in the gaze-position (cursor) is smoothed and a rapid change in the gaze-position caused by a blink is reduced.

Further, there is a technique disclosed by "Full-time Wearable Headphone-Type Gaze Detector", Interaction 2006, pages 23 to 24, 2006 (Non-Patent Literature 1), Hiroyuki Manabe, Masaaki Fukumoto, as a technique presenting an effect of the blink signal.

According to the technique disclosed in the Non-Patent reference 1, a total of 8 electrodes are placed on the right and left of a headphone. A median filter is applied at 0.4 second intervals as to changes in the electro-oculogram obtained from the 8 electrodes, thereby removing a change caused by a blink signal that is shorter than the above-described time interval.

However, as shown in the Patent Literature 6, merely temporally smoothing the electro-oculogram original signal causes an adverse effect that the smoothing is performed even on a saccade waveform indicating a component change in a saccade (a rapid movement of a human eye from one gaze-point to another gaze-point (saccadic movement)) that is important in tracking a gaze-path.

In addition, when a median filter is applied to the electro-oculogram original signal as shown in the Non-Literature reference 1, although a blink signal that has been generated singly can be removed as shown in FIG. 22, the effects of blink signals that have been generated continuously for at least a predetermined amount of time cannot be completely removed. In addition, an adverse effect that a part of the saccade waveform breaks is caused.

Therefore, the above-described references have not made it clear what smoothing filter should be applied how long and in what order is optimum, in consideration of removal of the blink signal and retaining the saccade signal.

Thus, in Embodiments 6 to 8, a method for removing or detecting a blink signal from an electro-oculogram signal of a user with ease and high accuracy, and further detecting a saccade signal will be described.

Embodiment 6

Figure 23:
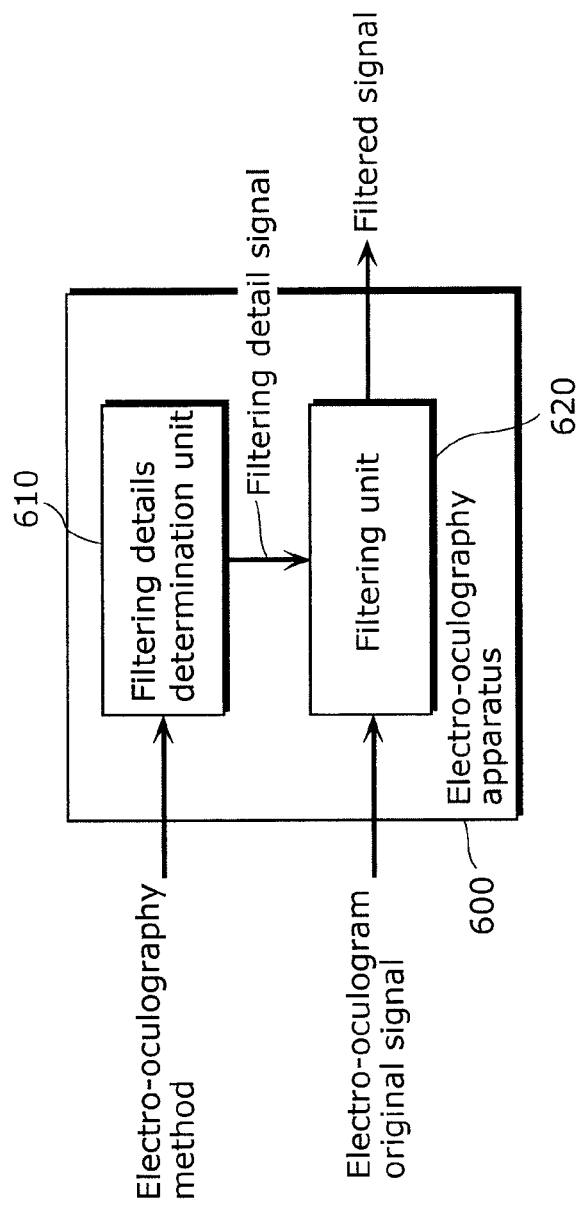
FIG. 23 is a block diagram of an electro-oculography apparatus according to Embodiment 6.

FIG. 23 is a block diagram that shows a structure of an electro-oculography apparatus 600 according to the Embodiment 6 of the present invention.

The electro-oculography apparatus 600 includes: an electro-oculogram measuring unit (illustration omitted) placed around a user's eye to measure an electro-oculogram and output an electro-oculogram original signal; a filtering detail determination unit 610 that determines a detail of filtering using a signal indicating how to measure the electro-oculogram (in the diagram: electro-oculography method); and a filtering unit 620 that performs filtering on the electro-oculogram original signal according to a filtering detail signal output from the filtering details determination unit 610.

First, the method of measuring the electro-oculogram may be specified in advance by an experimenter or a user, or may be estimated based on a tendency of change in the electro-oculogram original signal.

More specifically, the user may specify a measuring method as the one that places electrodes A and B on the right and left, respectively, of an eyeball as shown in FIGS. 36A and 36B, or when a signal is generated upward in the electro-oculogram original signal whenever the user blinks, it may be estimated that the placement pattern as shown in FIG. 20A and FIG. 20B is employed for the measuring method.

Figure 24:
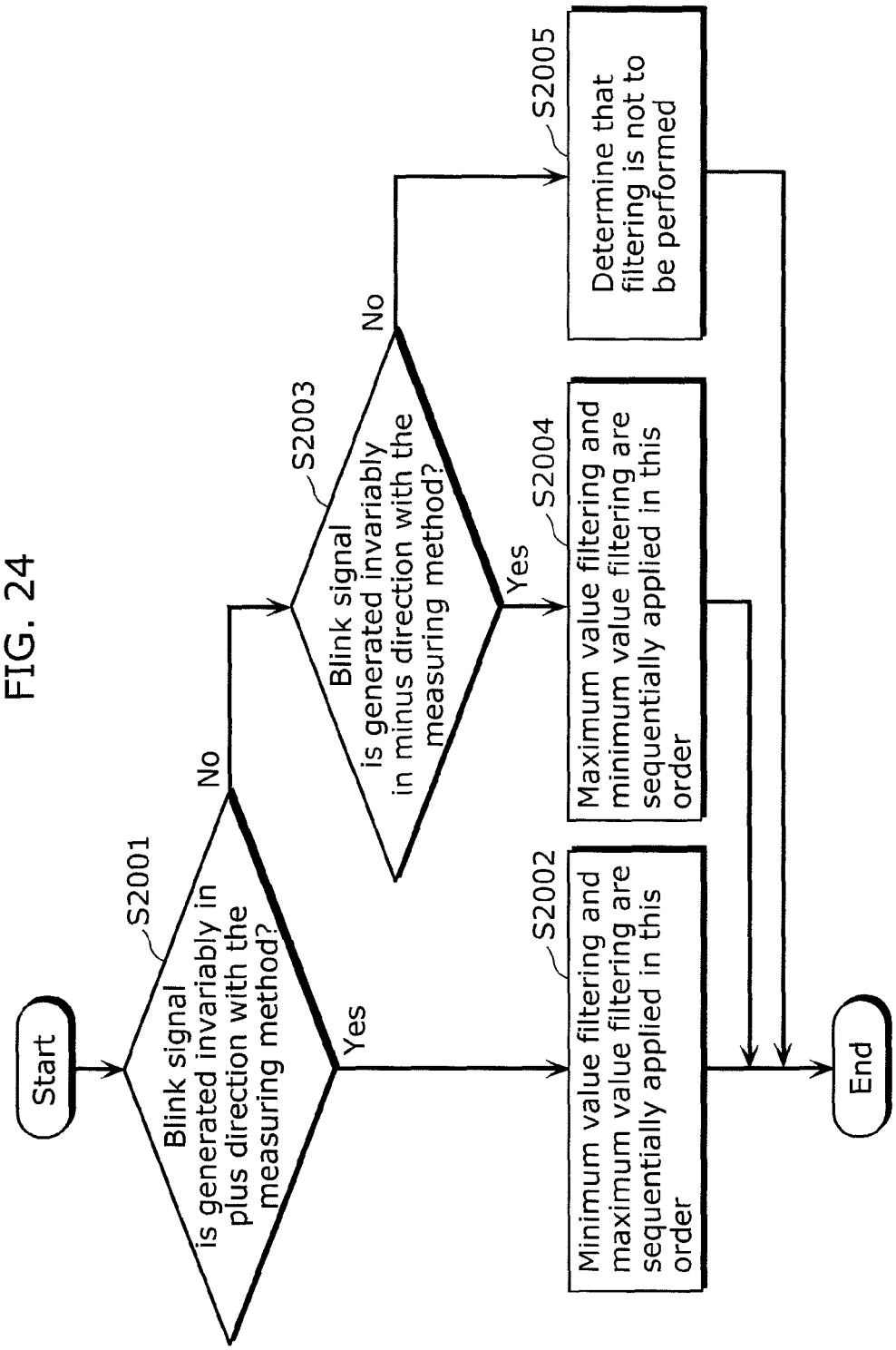
FIG. 24 is a flow chart that shows operations of a filtering detail determination unit.

FIG. 24 is a flow chart that shows operations of the filtering detail determination unit 610. The filtering detail determination unit 610 determines an order of applying a filter (described later) in the filtering unit 620 to first remove an effect of a blink. Further, although not shown, the number of necessary taps (time) is determined depending on the difference of electro-oculography methods. Furthermore, whether or not a filter is to be applied changes depending on whether the electrodes placed in advance are placed in a horizontal direction or in a vertical direction.

More specifically, it is determined whether or not a blink signal is generated invariably in the plus direction with the measuring method as in the placement pattern of FIG. 20A and FIG. 20B (Step S2001). When the blink signal indicates invariably a plus potential (Yes in Step S2001), a filtering detail is determined so that the minimum value filtering and the maximum value filtering are performed in this order (Step S2002).

Figure 20C:
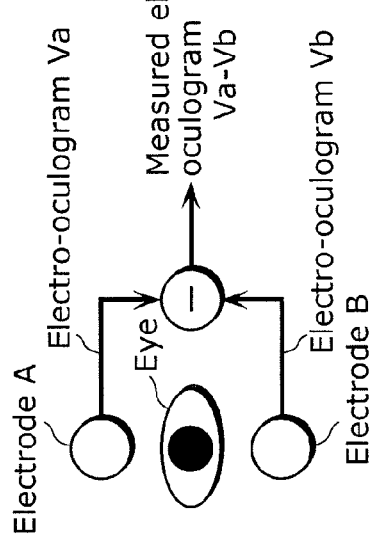
FIG. 20C is a diagram that shows another example of the pattern of attaching electrodes.
Figure 20D:
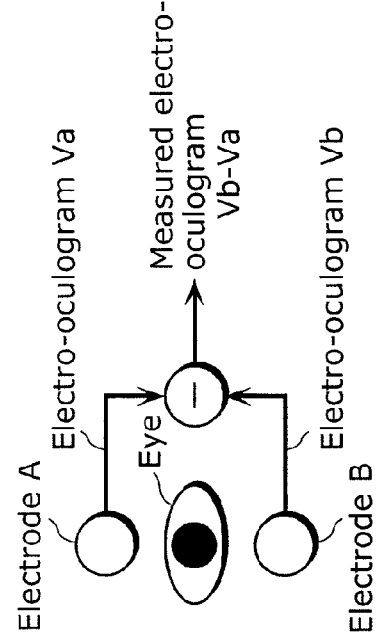
FIG. 20D is a diagram that shows another example of the pattern of attaching electrodes.

When the blink signal does not indicate a plus potential (No in Step S2001), it is determined whether or not the blink signal is generated invariably in the minus direction with the measuring method as in the placement pattern of FIG. 20C and FIG. 20D (Step S2003). When the blink signal indicates invariably the minus potential (Yes in Step S2003), a filtering detail is determined so that the maximum value filtering and the minimum value filtering are performed in this order (Step S2004).

When the blink signal does not indicate a minus potential (No in Step S2003), it is determined that the measuring method is not affected by a blink, and that filtering is not to be performed for removing a blink signal (Step S2005). It is to be noted that, an example of the case where the measuring method is not affected by a blink includes: the case where electrodes A and B are placed on the right and on the left of an eye, respectively, as shown in FIG. 36A and FIG. 36B to measure the difference; and the case where electrodes A and B are placed away from an eye.

The filtering detail determination unit 610 outputs a filtering detail signal (orientation, the number of tap n, presence or absence (n=0 may also be output)) by including information such as an application order of the filter which has been determined in the above process, the number of tap n of the filter, and unit processing period. It is to be noted that the determination order of the above-described flow chart is an example, and any determination order may be employed.

Figure 25:
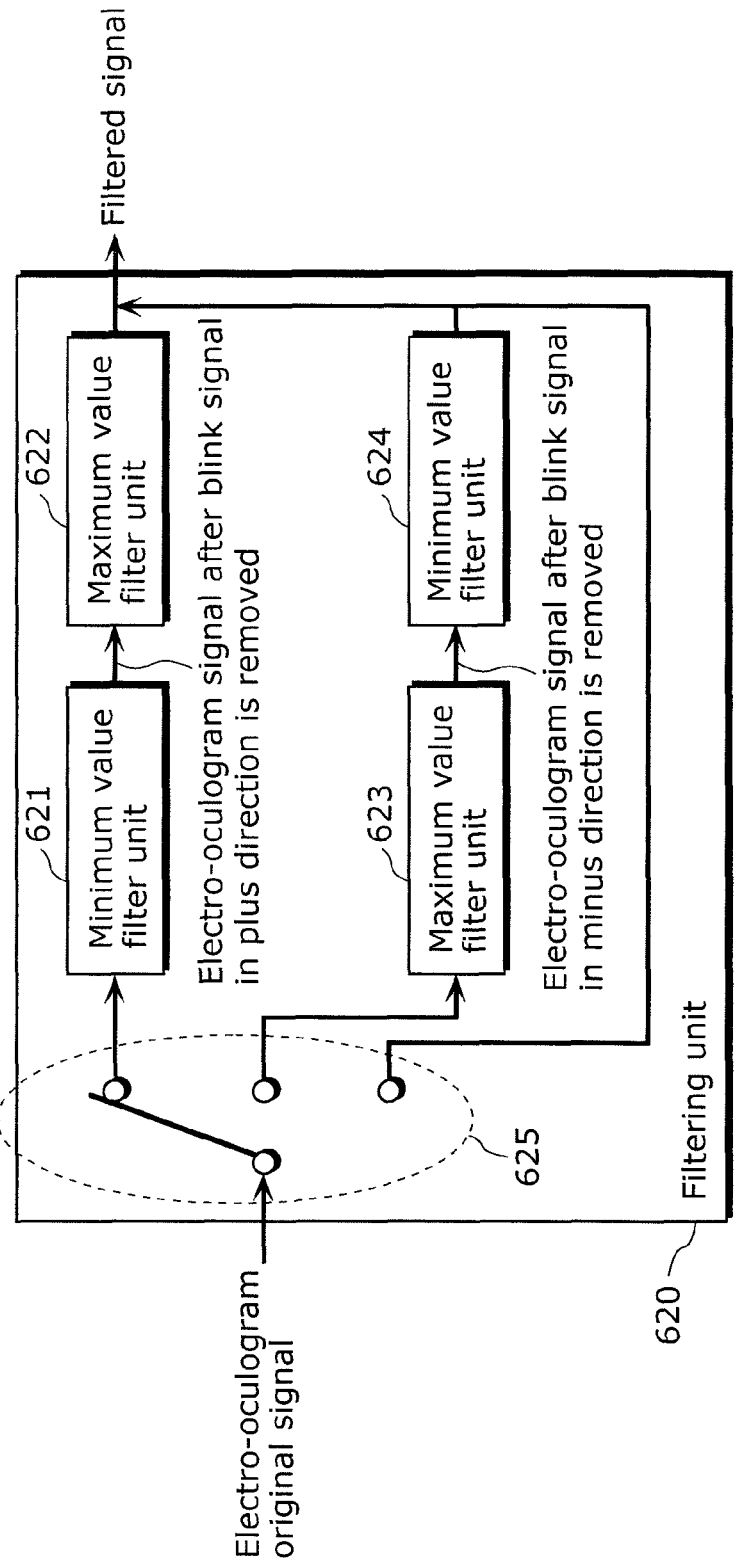
FIG. 25 is a block diagram of the filtering unit of FIG. 23.

FIG. 25 is a diagram that shows a structure of the filtering unit 620. The filtering unit 620 performs filtering on the electro-oculogram original signal according to the filtering details signal that has been output from the filtering detail determination unit 610.

The filtering unit 620 includes: two minimum value filter units 621 and 624; two maximum value filter units 622 and 623; and a switch 625 that switches between the first path to the third path from an input terminal to an output terminal to connect one of the paths to which the electro-oculogram original signal is output.

In the first path, the minimum value filter unit 621 (the first filtering unit) and the maximum value filter unit 622 (the second filtering unit) are connected in series, in which the minimum value filter unit 621 performs the minimum value filtering on the electro-oculogram original signal and outputs a first electro-oculogram signal, and the maximum value filter unit 122 performs the maximum value filtering on the first electro-oculogram signal and outputs a second electro-oculogram signal (filtered signal). In the second path, the maximum value filter unit 623 (the first filtering unit) and the minimum value filter unit 624 (the second filtering unit) are connected in series, in which the maximum value filter unit 623 performs the maximum value filtering on the electro-oculogram original signal and outputs a first electro-oculogram signal, and the minimum value filter unit 624 performs the minimum value filtering on the first to electro-oculogram signal and outputs a second electro-oculogram signal (filtered signal). The third path is a path that outputs the electro-oculogram original signal without performing filtering processing. The switch 625 switches output destinations to which the electro-oculogram original signal is output, according to the filtering detail determined by the filtering detail determination unit 610.

In the case where the switch 625 receives the filtering detail signal generated in Step S2002 shown in FIG. 24, the switch 625 switches a connection point to the one in the top stage shown in FIG. 25, so that the electro-oculogram original signal is output to the first path. Further, in the case where the switch 625 receives a filtering detail signal generated in Step S2004 shown in FIG. 24, the switch 625 switches the connection point to the one in the middle stage shown in FIG. 25, so that the electro-oculogram original signal is output to the second path. Furthermore, in the case where the switch 625 receives a filtering detail signal generated in Step S2005 shown in FIG. 24, the switch 625 switches the connection point to the one in the bottom stage shown in FIG. 25, so that the electro-oculogram original signal is output to the third path.

It is to be noted that, the processing details of the minimum value filter units 621 and 624, and the maximum value filter units 622 and the 623 are the same as those described in the Embodiment 2. It is to be noted that, although two units are included in each of the minimum value filter unit and the maximum value filter unit, that is, the minimum value filter units 621 and 624 and the maximum value filter units 622 and 623, it is also possible to provide a single unit for each of the minimum value filter unit and the maximum value filter unit and change an order of connection based on the filtering detail signal, and the like, to achieve the invention.

Next, processing in the case where the electro-oculogram original signal is inputted into the first path will be described. First, FIG. 26 is a diagram that shows the first electro-oculogram signal obtained by performing, on the electro-oculogram original signal as shown in FIG. 21, the minimum value filtering in the minimum value filter unit 621.

It is to be noted that, in order to remove the blink signal from the electro-oculogram original signal, the unit processing period of the minimum value filter unit 621 is set to 0.25 seconds in accordance with the value determined with a filtering detail signal.

Figure 26:
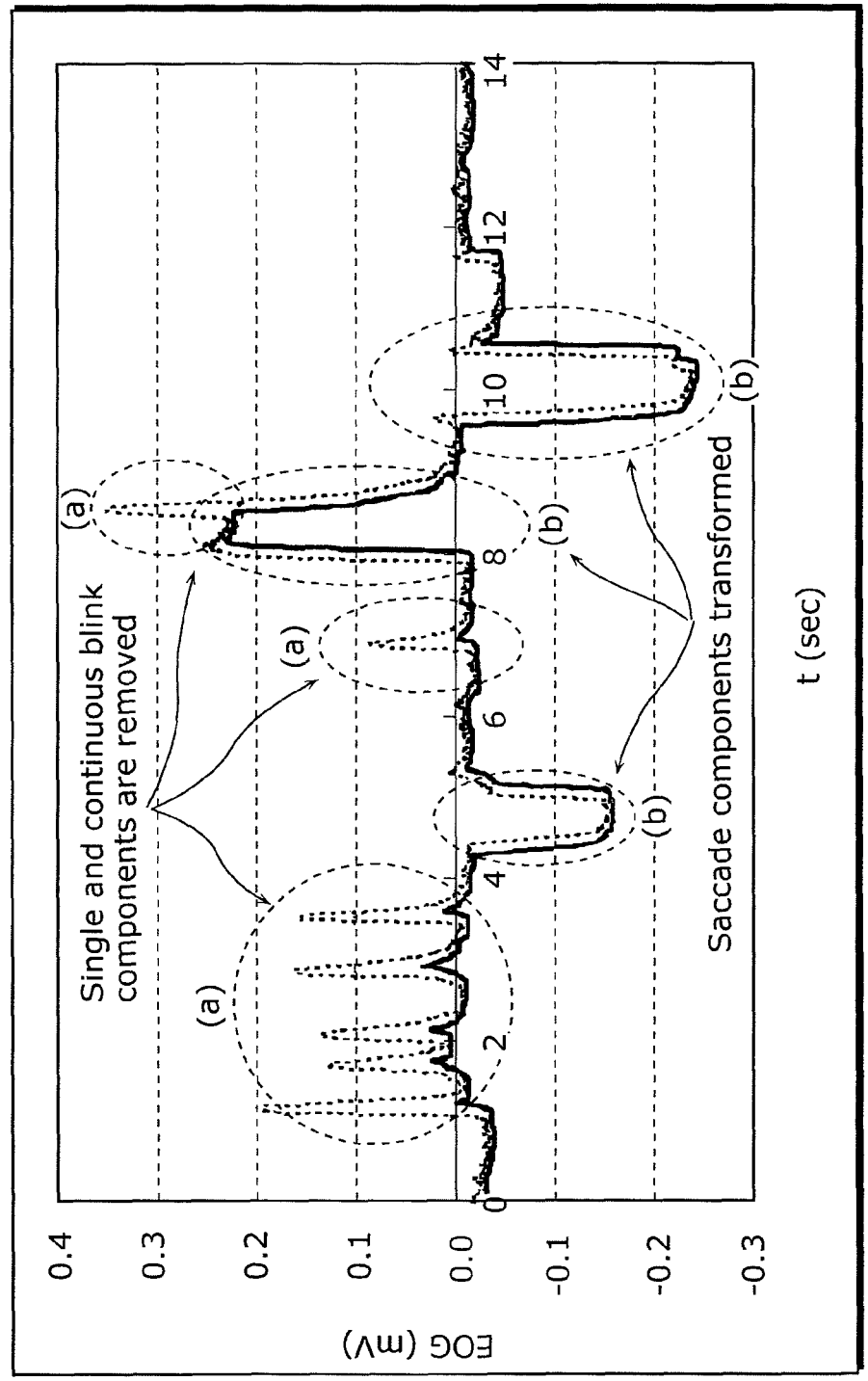
FIG. 26 is a diagram that shows an electro-oculogram signal obtained by applying the minimum value filtering on the electro-oculogram signal of FIG. 21.

It can be understood by referring to regions (a) in FIG. 26 that consecutive blink signals and an isolated blink signal is removed by performing the minimum value filtering on the electro-oculogram original signal. However, in the first electro-oculogram signal as shown in FIG. 26, the saccade waveforms have transformed (increased in a temporal width), which is an adverse effect caused by performing the minimum value filtering.

It is to be noted that, although the Embodiment 6 has presented an example where the minimum value filtering is performed by setting the unit processing period of the minimum value filter unit 621 to 0.25 seconds, it may be any value as long as it is longer than a general duration of a single blink=(from 0.15 seconds to 0.2 seconds, approximately) and shorter than a single fixation time=(from 0.3 seconds to 0.4 seconds, approximately).

Figure 27:
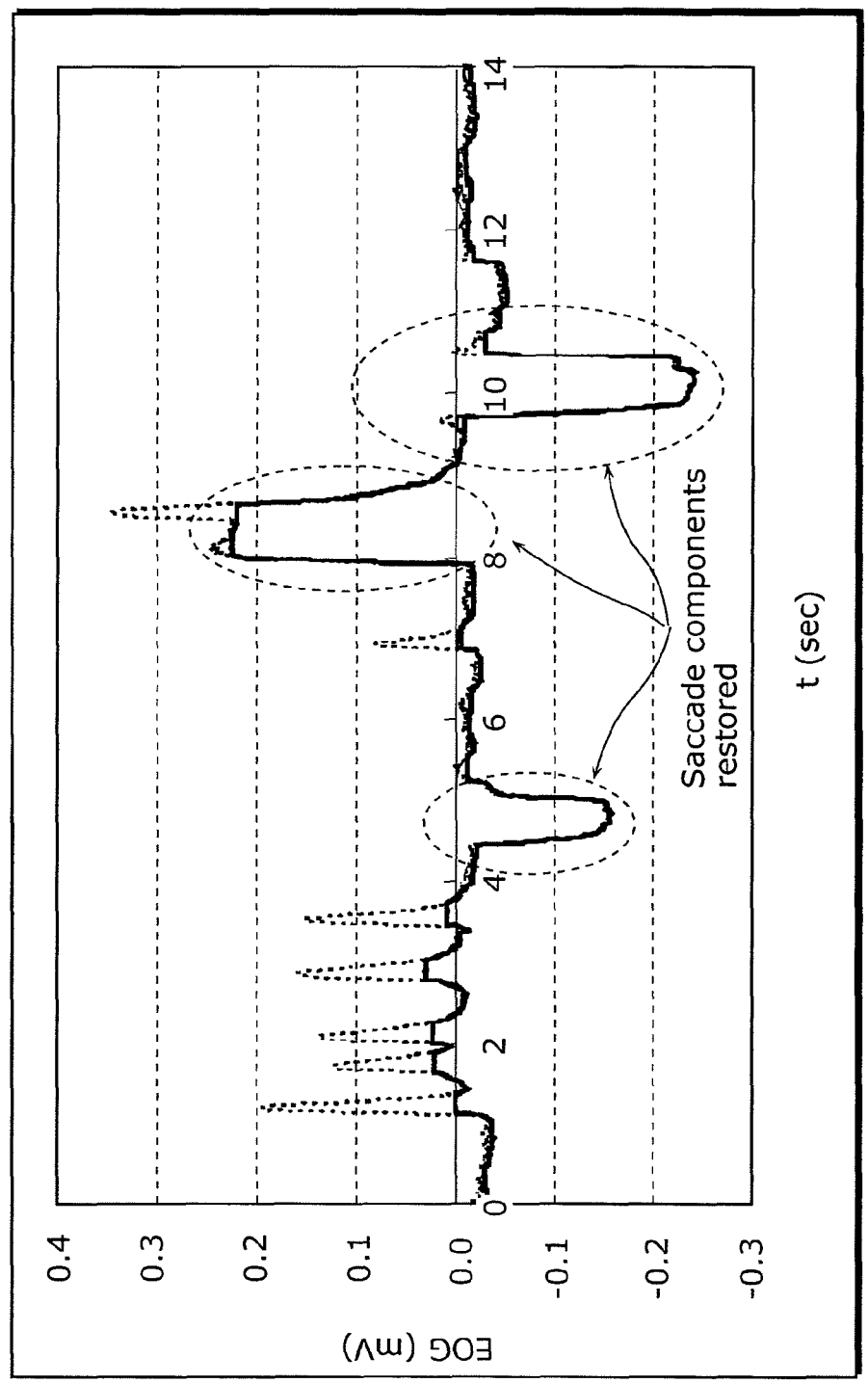
FIG. 27 is a diagram that shows an electro-oculogram signal obtained by applying the maximum value filtering on the electro-oculogram signal of FIG. 26.

Next, FIG. 27 is a diagram that shows a second electro-oculogram signal (filtered signal) obtained by performing the maximum value filtering, on the first electro-oculogram signal as shown in FIG. 26, in the maximum value filter unit 622. It is to be noted that, the unit processing period is set to 0.25 seconds as in the case of the minimum value filtering unit 621.

As shown in FIG. 27, the transformed saccade waveform as in FIG. 26 can be restored to the original signal waveform by performing the maximum value filtering on the first electro-oculogram signal.

Fundamental processes of the maximum value filter unit 623 and the minimum value filter unit 624 are the same as the maximum value filter unit 622 and the minimum value filter unit 621, respectively, and it is possible to remove the blink signal in the minus direction without affecting the saccade waveform, by performing filtering in order of the maximum value filtering and the minimum value filtering.

It is to be noted that, although the minimum value filter units 621 and 624, and the maximum value filter units 622 and 623 are used in the example of the Embodiment 6, a filter that selects a value close to the minimum value or the maximum value may be used. In this case, it is desirable to select a value approximately 90% of the maximum value or the minimum value.

Further, although the same value is used for the number of filter taps of the minimum value filtering and the maximum value filtering in the Embodiment 6, a proximate value may be used. In other words, perfect matching is not necessarily required.

In the case where plural filtering processes are performed consecutively, it is sufficient to perform the filtering for removing the effect of the blink signal first, and then perform the filtering for restoring the temporal waveform of saccade.

Further, although the blink signal is removed and the saccade waveform is restored by consecutively performing the minimum value filtering and the maximum value filtering in the Embodiment 6, only one of the minimum value filtering and the maximum value filtering may be performed without departing from the scope of the present invention when the purpose is only to remove the blink signal.

According to the structure of the above-described Embodiment 6, the detail of filtering to be performed on an electro-oculogram original signal is determined according to the method of measuring the electro-oculogram original signal, and filtering is performed according to the detail. As a result, it is possible to remove a blink signal properly, even when the electrodes are placed in the opposite orientation, for example.

Further, when the measuring method is such that a blink signal is generated in the plus direction of an electro-oculogram original signal, a filtering detail is determined such that the minimum value filtering and the maximum value filtering are performed consecutively in this order. As a result, it is possible to easily remove a blink signal in the plus direction and restore a saccade waveform.

Further, when the measuring method is such that a blink signal is generated in the minus direction of an electro-oculogram original signal, a filtering detail is determined such that the maximum value filtering and the minimum value filtering are performed consecutively in this order. As a result, it is possible to easily remove a blink signal in the minus direction and restore a saccade waveform.

The electro-oculography apparatus 600 having the above-described structure can be applied to the eye gaze tracking apparatus 100 shown in FIG. 1. A filtering processing signal that is output from the electro-oculography apparatus 600 is input to the switch 106 shown in FIG. 1 as an electro-oculogram original signal, for example. This eliminates the need to take a blink signal into consideration in the calibration unit 101 and the saccade detection unit 104 even when an electro-oculogram signal including the blink signal is measured in the electro-oculogram measuring unit.

Embodiment 7

Figure 28:
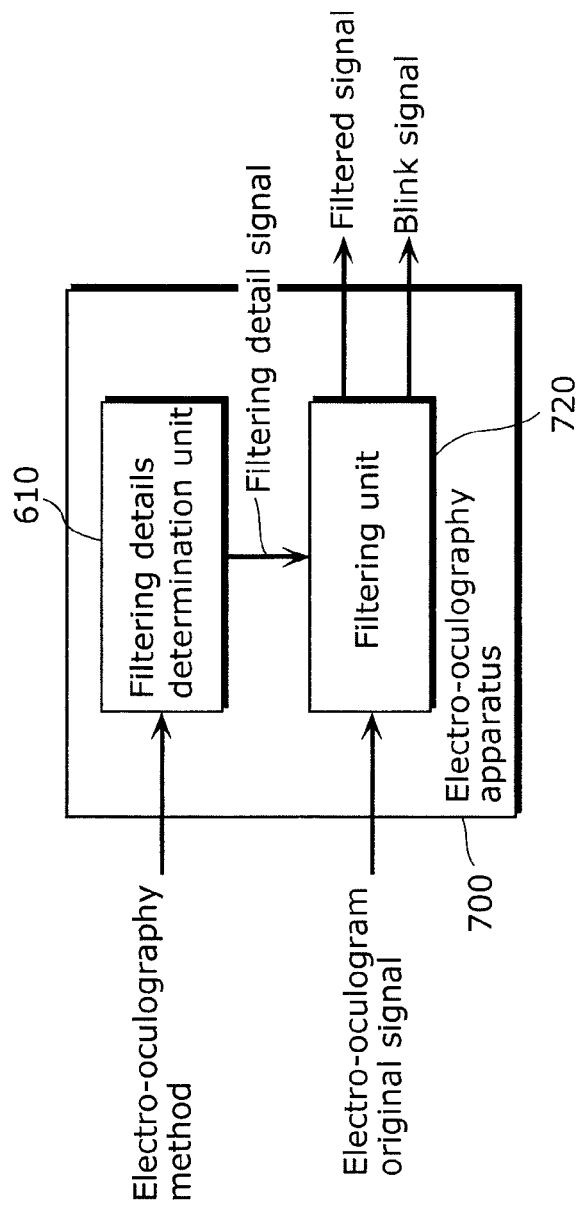
FIG. 28 is a block diagram of an electro-oculography apparatus according to Embodiment 7.
Figure 29:
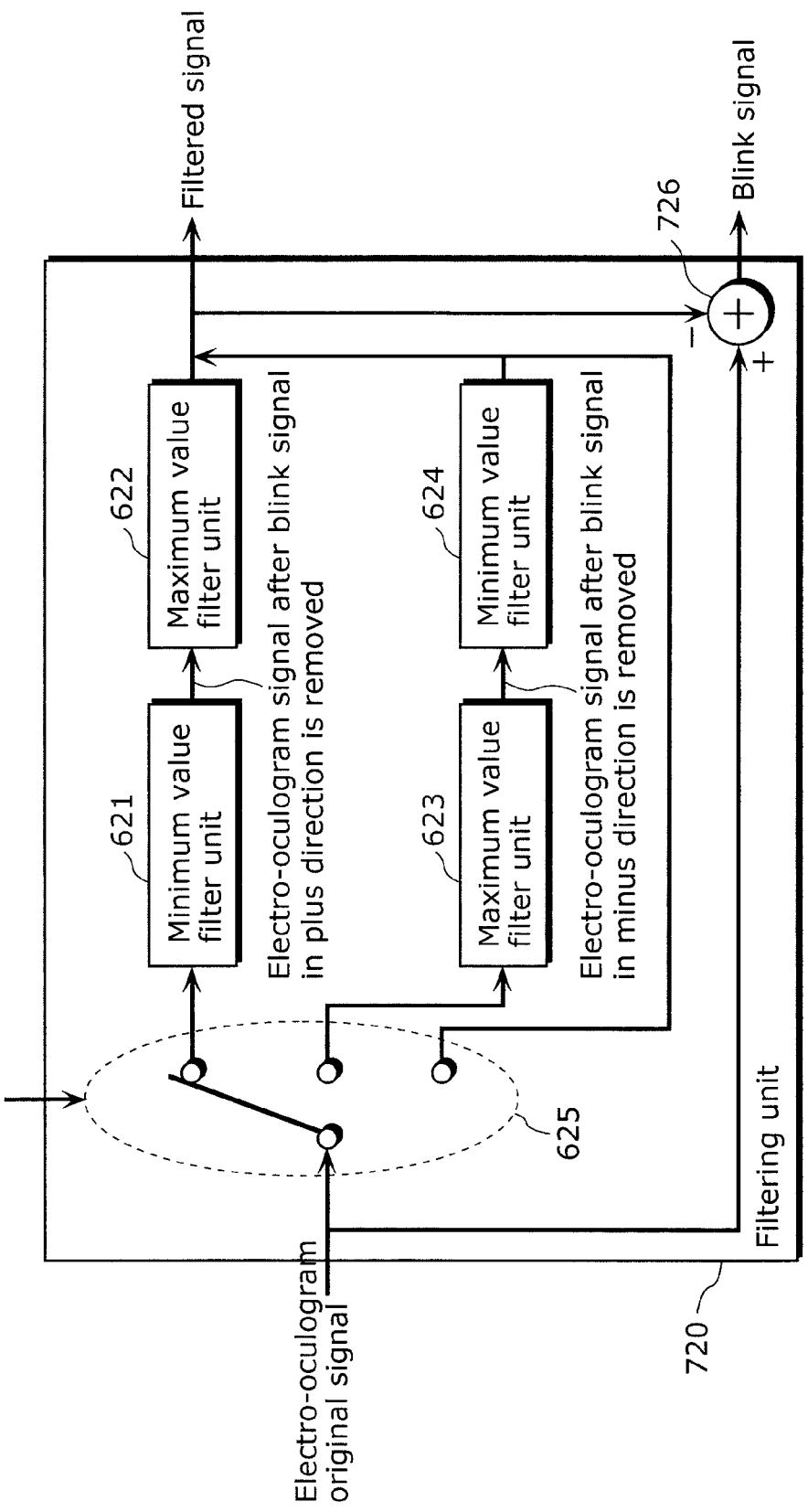
FIG. 29 is a block diagram of the filtering unit of FIG. 28.

FIG. 28 and FIG. 29 are block diagrams which shows a structure of an electro-oculography apparatus 700 according to Embodiment 7 of the present invention.

The Embodiment 7 differs from the Embodiment 6 in that a filtering unit 720 includes a subtraction unit 726 that subtracts a filtered electro-oculogram signal from the electro-oculogram original signal. The inclusion of the subtraction unit 726 makes it possible to output a blink signal in addition to the filtered signal.

FIG. 29 is a block diagram which shows an example of filtering unit 720 in the electro-oculography apparatus 700 according to the Embodiment 7. It is to be noted that, since the structure same as the structure in FIG. 25 has already been described, the same numerals are assigned and the description that is overlapped will be omitted.

The subtraction unit 726 outputs a difference between the electro-oculogram original signal and the filtered signal. The difference is a blink signal.

Figure 30:
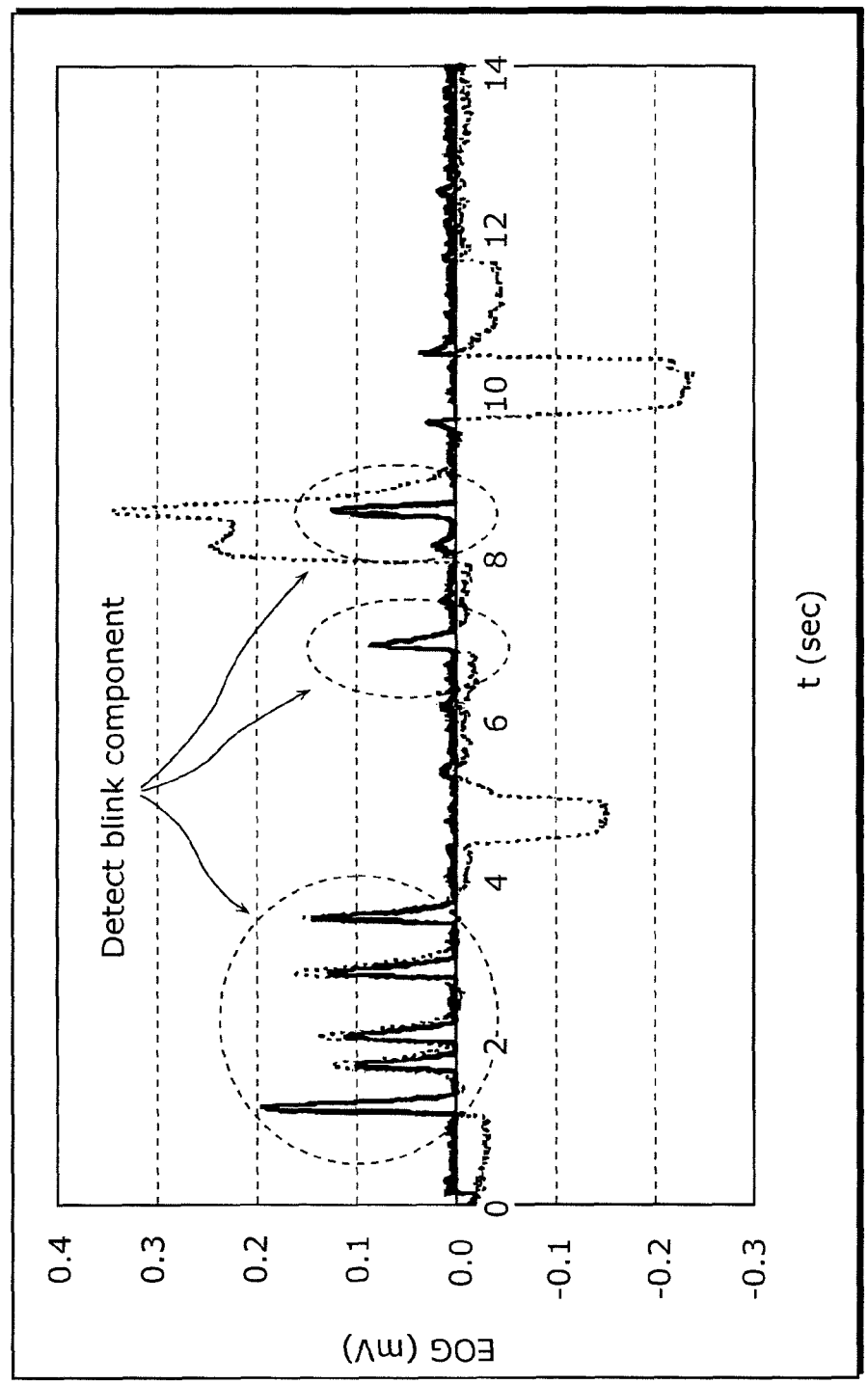
FIG. 30 is a diagram that shows a blink signal obtained by inputting the electro-oculogram signal of FIG. 26 into the filtering unit of FIG. 29.

FIG. 30 shows a blink signal obtained by subtracting the second electro-oculogram signal in FIG. 27 from the electro-oculogram original signal in FIG. 21. It is understood, by referring to FIG. 30, that only the blink signal is detected from the electro-oculogram original signal.

According to the structure of the above-described Embodiment 7, the detail of filtering to be performed on an electro-oculogram original signal is determined according to the method of measuring the electro-oculogram original signal, and suitable filtering is performed according to the detail. As a result, it is possible to detect a blink signal no matter what a measuring method is employed.

Further, when the measuring method is such that a blink signal is generated in the plus direction of an electro-oculogram original signal, a filtering detail is determined such that the minimum value filtering and the maximum value filtering are performed consecutively in this order. As a result, it is possible to restore a saccade component while easily detecting the blink signal in the plus direction.

Further, when the measuring method is such that a blink signal is generated in the minus direction of an electro-oculogram original signal, a filtering detail is determined such that the maximum value filtering and the minimum value filtering are performed consecutively in this order. As a result, it is possible to restore a saccade component while easily detecting the blink signal in the minus direction.

Embodiment 8

Figure 31:
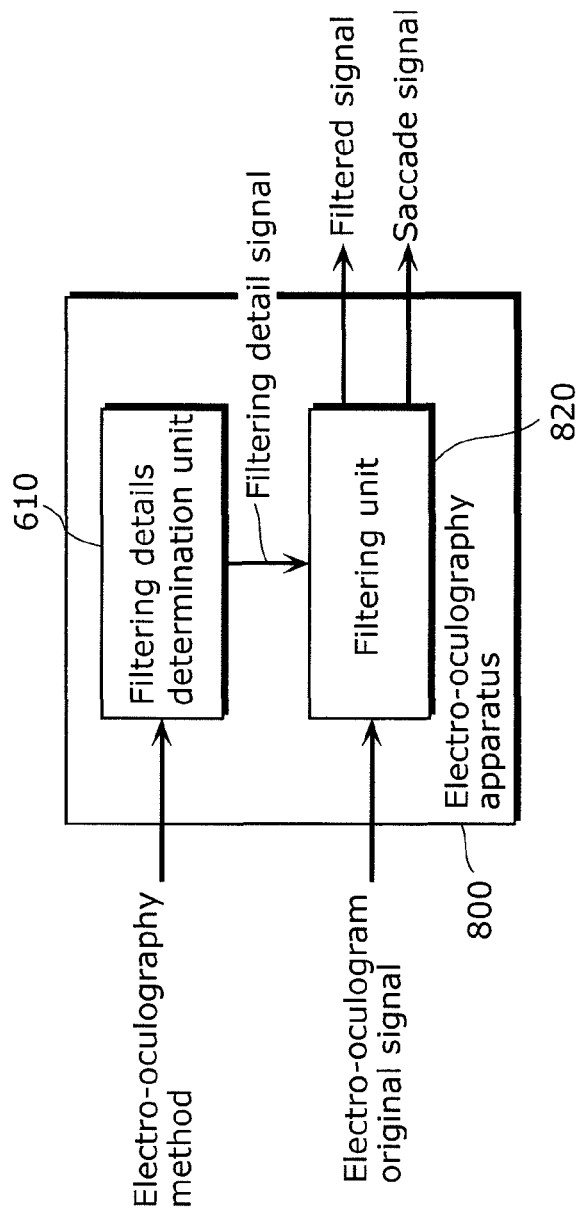
FIG. 31 is a block diagram of an electro-oculography apparatus according to Embodiment 8.
Figure 32:
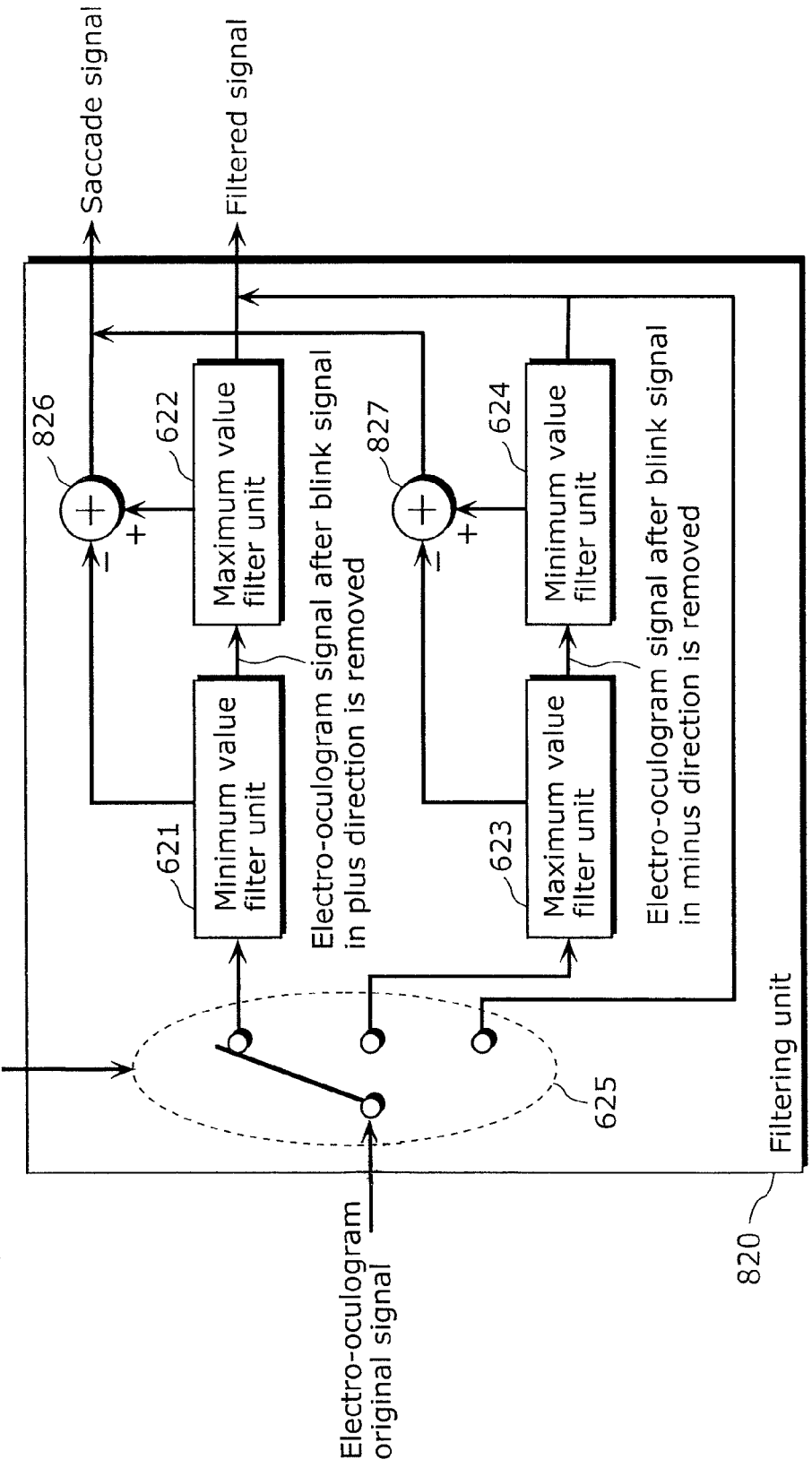
FIG. 32 is a block diagram of the filtering unit of FIG. 31.

FIG. 31 and FIG. 32 are block diagrams which show a structure of an electro-oculography apparatus 800 according to Embodiment 8 of the present invention.

The Embodiment 8 differs from the Embodiment 6 in that a filtering unit 820 includes subtraction units 826 and 827 which subtract a signal on which one of the maximum value filtering or the minimum value filtering has been performed (a first electro-oculogram signal) from a signal on which both of the maximum value filtering and the minimum value filtering have been performed (a second electro-oculogram signal). The inclusion of the subtraction units 826 and 827 makes it possible to output a saccade signal in addition to the filtered signal.

FIG. 32 is a block diagram which shows an example of filtering unit 820 in the electro-oculography apparatus 800 according to the Embodiment 8. It is to be noted that, since the structure same as the structure in FIG. 25 has already been described, the same numerals are assigned and the description that is overlapped will be omitted.

The subtraction unit 826 outputs a saccade signal by subtracting an output signal of the minimum value filter unit 621 from an output signal of the maximum value filter unit 622. Similarly, the subtraction unit 827 outputs a saccade signal by subtracting an output signal of the maximum value filter unit 623 from an output signal of the minimum value filter unit 624.

Figure 33:
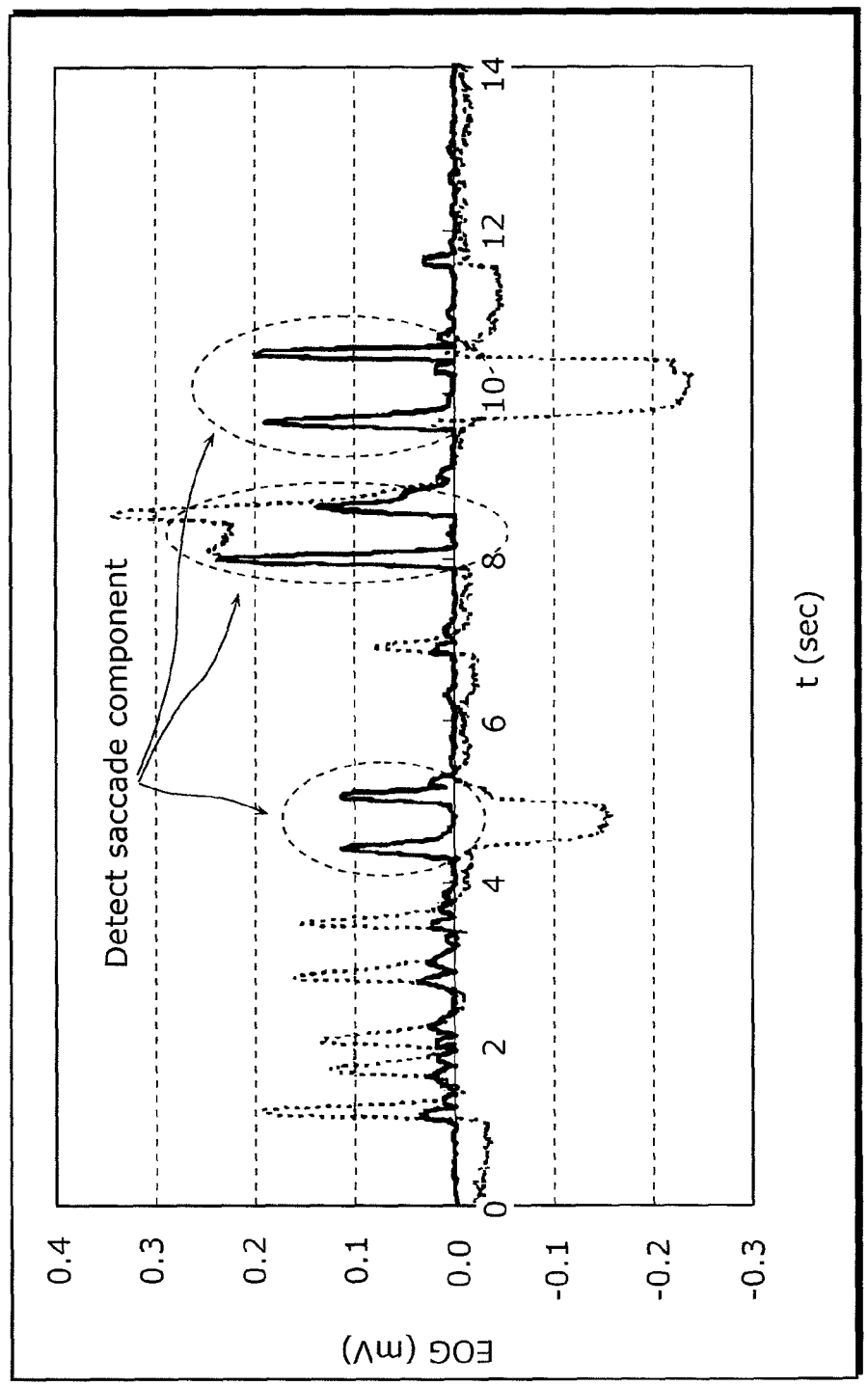
FIG. 33 is a diagram that shows a saccade signal obtained by inputting the electro-oculogram signal of FIG. 26 into the filtering unit of FIG. 32.

FIG. 33 shows a saccade signal obtained by subtracting the first electro-oculogram signal in FIG. 26, on which the minimum value filtering has been performed, from the second electro-oculogram signal in FIG. 27, on which the maximum value filtering has been performed. It is understood, by referring to FIG. 33, that only the saccade signal is detected from the electro-oculogram original signal.

According to the structure of the above-described Embodiment 8, the detail of filtering to be performed on an electro-oculogram original signal is determined according to the method of measuring the electro-oculogram original signal, and filtering is performed according to the detail. As a result, it is possible to detect a saccade signal no matter what a measuring method is employed. More specifically, it is possible to properly detect a saccade without being affected by a blink signal, by applying the filtering unit 820 to the saccade detection unit 104 shown in FIG. 1.

Further, when the measuring method is such that a blink signal is generated in the plus direction of an electro-oculogram original signal, a filtering detail is determined such that the minimum value filtering and the maximum value filtering are performed consecutively in this order, and further that the first electro-oculogram signal on which the minimum value filtering has been performed is subtracted from the second electro-oculogram signal on which the maximum value filtering has been performed. As a result, it produces an advantageous effect that the saccade signal can be detected while removing the blink signal of the plus direction.

Further, in the Embodiment 8, there is an advantageous effect that it is possible to detect a saccade signal including a generation time of the saccade signal by setting the number of filter taps of the maximum value filtering to be greater than the number of filter taps of the minimum value filtering.

On the other hand, when the measuring method is such that a blink signal is generated in the minus direction of an electro-oculogram original signal, a filtering detail is determined such that the maximum value filtering and the minimum value filtering are performed consecutively in this order, and further that the first electro-oculogram signal on which the maximum value filtering has been performed is subtracted from the second electro-oculogram signal on which minimum value filtering has been performed. As a result, it produces an advantageous effect that the saccade signal can be detected while removing the blink signal in the minus direction. In this case, the saccade signal appears invariably in the minus direction (the waveform is reversed from the one in FIG. 33). Therefore, it is necessary to add a process to invert plus and minus in order to obtain a signal as shown in FIG. 33. On the other hand, in the case where the saccade signal is used only for detecting a generation timing of the saccade, there is no need to invert plus and minus.

Further, in the Embodiment 8, there is an advantageous effect that it is possible to detect a saccade signal including a generation time of the saccade signal by setting the number of filter taps of the minimum value filtering to be greater than the number of filter taps of the maximum value filtering.

It is to be noted that, removing a blink signal, detecting a blink signal, or detecting a saccade signal has been focused in each of the above-described Embodiments 6 to 8, and the number of the filter taps of filtering to be performed first between the minimum value filtering and the maximum value filtering has been described. The number of the filter taps may be used for removing a muscle potential, a noise, and the like, by being adjusted to the muscle potential, the noise, and the like.

Embodiment 9

Figure 34:
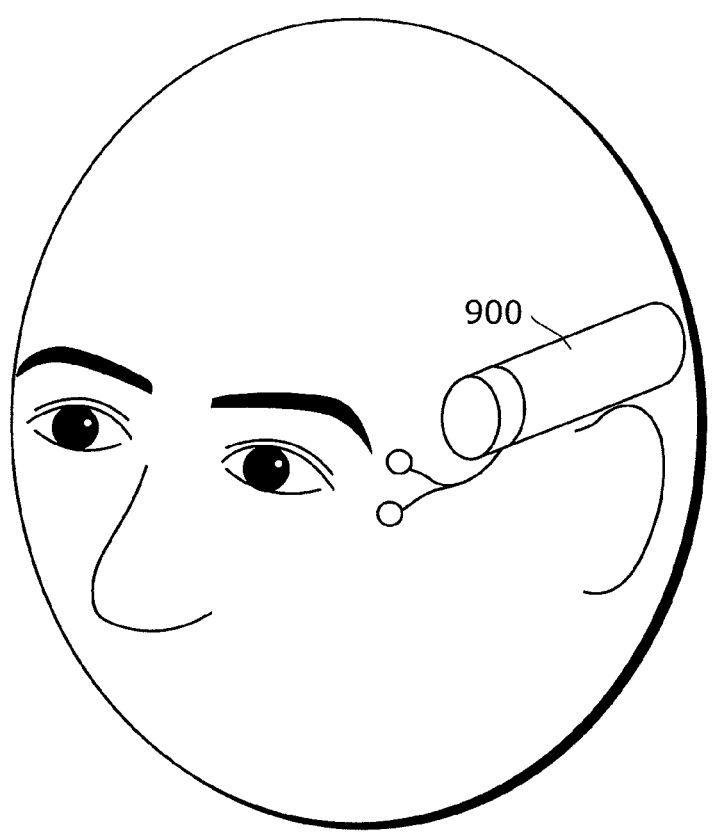
FIG. 34 is a diagram that shows an imaging apparatus according to Embodiment 9 which is worn by a user.
Figure 35:
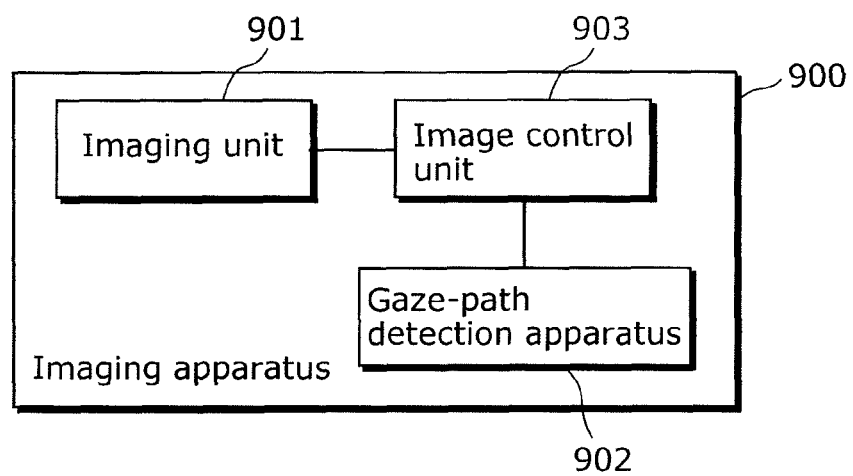
FIG. 35 is a block diagram of an imaging apparatus according to Embodiment 9.

Next, an imaging apparatus 900 according to Embodiment 9 of the present invention will be described with reference to FIG. 34 and FIG. 35. The imaging apparatus 900 is worn by a user on a temporal part, and images a gaze direction of the user. More specifically, the imaging apparatus 900 includes an imaging unit 901, an eye gaze tracking apparatus 902, and an image control unit 903.

The imaging unit 900 may be a camera that takes a still picture, or may be a video camera the shoots a moving image, for example. The eye gaze tracking apparatus 100 according to the Embodiment 1 may be applied to the eye gaze tracking apparatus 900, for example. Further, an electrode that is an electro-oculogram measuring unit in the Embodiment 9 is placed above and below the left temple of the user as shown in FIG. 34.

Then, the image control unit 903 monitors an output signal from the eye gaze tracking apparatus 902 and changes an orientation of the imaging unit 901 according to the movement of a gaze-path of the user. This allows the imaging unit 901 to take an image of the gaze path direction of the user.

However, the eye gaze tracking apparatus 100 according to the Embodiment 1 is not limited to the above application. Other applications include an application into an apparatus that plots a gaze-point of a user detected by the eye gaze tracking apparatus 100 on an image captured by the imaging apparatus.

Other Modifications

It should be understood that, although the present invention has been described according to each of the Embodiments 1 to 9 described above, the present invention is not limited to each of the Embodiments 1 to 9 described above. The present invention includes cases below.

(1) Each device mentioned above is, to be specific, a computer system that includes a microprocessor, a ROM, a RAM, a hard disk unit, a display unit, a keyboard, a mouse, and so on. A computer program is stored on the RAM or the hard disk unit. The microprocessor operates according to the computer program, so that each device achieves its function. Here, the computer program is configured by combining plural instruction codes indicating instructions for a computer in order to implement a predetermined function.

(2) A part or all of the constituent elements constituting the respective apparatuses may be configured from a single System-LSI (Large-Scale Integration). The System-LSI is a super-multi-function LSI manufactured by integrating constituent units on one chip, and is specifically a computer system configured by including a microprocessor, a ROM, a RAM, and so on. A computer program is stored in the RAM. The System-LSI achieves its function through the microprocessor's operation according to the computer program.

(3) A part or all of the constituent elements included in the respective apparatuses may be configured as an IC card which can be attached and detached from the respective apparatuses or as a stand-alone module. The IC card or the module is a computer system configured from a microprocessor, a ROM, a RAM, and so on. The IC card or the module may also include the aforementioned super-multi-function LSI. The IC card or the module achieves its function through the microprocessor's operation according to the computer program. The IC card or the module may also be implemented to be tamper-resistant.

(4) The present invention may be a method as described above. Further, the present invention may be a computer program for realizing the above-described method using a computer, and may also be a digital signal including the computer program.

Furthermore, the present invention may also be realized by storing the computer program or the digital signal in a computer readable recording medium such as flexible disc, a hard disk, a CD-ROM, an MO, a DVD, a DVD-ROM, a DVD-RAM, a BD (Blu-ray Disc), and a semiconductor memory. Furthermore, the present invention also includes the digital signal recorded in these recording media.

Furthermore, the present invention may also be realized by the transmission of the aforementioned computer program or digital signal via a telecommunication line, a wireless or wired communication line, a network represented by the Internet, a data broadcast and so on.

The present invention may also be a computer system including a microprocessor and a memory, in which the memory stores the aforementioned computer program and the microprocessor operates according to the computer program.

Furthermore, by transferring the program or the digital signal by recording onto the aforementioned recording media, or by transferring the program or digital signal via the aforementioned network and the like, execution using another independent computer system is also made possible.

(5) Each of the above-mentioned embodiments may be applied to each of the above-described modification examples.

Embodiments of according to the present invention have been described with reference to the drawings. However, the present invention is not limited to the embodiments that have been illustrated. It is possible to apply various corrections and modifications to the embodiments that have been illustrated, within the same or equivalent scope of the present invention.

INDUSTRIAL APPLICABILITY

The present invention is useful as a device and the like which record and reproduce an image or a voice in areas including broadcasting, communication, and storage. Further, the present invention can also be implemented as a still picture record and reproduction device and so on. Furthermore, the present invention can also be implemented as a health and medical device.

REFERENCE SIGNS LIST 10 display
20 first calibration index
30 second calibration index
100, 902 eye gaze tracking apparatus
101 calibration unit
102 calibration parameter update instruction unit
103 calibration index presenting unit
104, 200, 300, 400, 500 saccade detection unit
105 calibration parameter calculating unit
106, 625 switch
201, 622, 623 maximum value filter unit
202, 621, 624 minimum value filter unit
203, 726, 826, 827 subtraction unit
501 delay signal generation unit
600, 700, 800 electro-oculography apparatus
610 filtering details determination unit
620, 720, 820 filtering unit
900 imaging apparatus
901 imaging unit
903 image control unit

The invention claimed is:

1. An eye gaze tracking apparatus which detects a gaze-path direction of a user from an electro-oculogram, said eye gaze tracking apparatus comprising:
   an electro-oculogram measuring unit configured to measure the electro-oculogram resulting from an eye movement, and to output an electro-oculogram original signal;
   a calibration index presenting unit configured to present a calibration index to the user;
   a saccade detection unit configured to (i) detect saccadic movements from the electro-oculogram original signal, each of the saccadic movements being a rapid eyeball movement which occurs when a gaze-point of the user moves to the calibration index presented by said calibration index presenting unit, and (ii) output an electro-oculogram change amount signal based on the detected saccadic movements, the electro-oculogram change amount signal indicating an amount of change, for each of the detected saccadic movements, between (a) a value of the electro-oculogram original signal prior to the detected saccadic movement and (b) a value of the electro-oculogram original signal at a time of the detected saccadic movement, the amount of change indicated by the electro-oculogram change amount signal reflecting a change in potential difference;
   a calibration parameter calculating unit configured to calculate a calibration parameter based on a position of the calibration index presented by said calibration index presenting unit and the electro-oculogram change amount signal that has been output from said saccade detection unit; and
   a calibration unit configured to detect the gaze-path direction of the user from the electro-oculogram original signal based on the calibration parameter.

2. The eye gaze tracking apparatus according to claim 1, wherein said saccade detection unit includes:
   a delay signal generation unit configured to delay the electro-oculogram original signal for a predetermined amount of time and output a delay signal;
   a subtraction unit configured to generate an output signal obtained by subtracting the delay signal from the electro-oculogram original signal; and
   a saccade determining unit configured to determine that a signal exceeding a predetermined threshold in the output signal is a saccade signal that indicates at least one of the saccadic movements.

3. The eye gaze tracking apparatus according to claim 2, wherein the predetermined amount of time of the delay is smaller than an amount of time of fixation by the user on the calibration index.

4. The eye gaze tracking apparatus according to claim 1, wherein said saccade detection unit includes:
   a first filtering unit configured to output a first electro-oculogram signal by performing one of maximum value filtering and minimum value filtering on the electro-oculogram original signal;
   a subtraction unit configured to subtract one of the first electro-oculogram signal and a second electro-oculogram signal from another of the first electro-oculogram signal and the second electro-oculogram signal, the second electro-oculogram signal being obtained from the electro-oculogram original signal; and
   a saccade determining unit configured to determine that a signal exceeding a predetermined threshold among the first electro-oculogram signal output from said first filtering unit and an output signal output from said subtraction unit is a saccade signal that indicates at least one of the saccadic movements.

5. The eye gaze tracking apparatus according to claim 4, wherein said saccade detection unit further includes a second filtering unit configured to output the second electro-oculogram signal by performing another of the maximum value filtering and the minimum value filtering on the electro-oculogram original signal.

6. The eye gaze tracking apparatus according to claim 4, wherein said saccade detection unit further includes a second filtering unit configured to output the second electro-oculogram signal by performing another of the maximum value filtering and the minimum value filtering on the first electro-oculogram signal.

7. The eye gaze tracking apparatus according to claim 1, wherein said calibration index presenting unit is configured to present a first calibration index to the user in response to receiving a calibration parameter update instruction, and then present a second calibration index at a position different from a position of the first calibration index in response to the detection of the saccadic movements by said saccade detection unit, and
   wherein said saccade detection unit is configured to output, to said calibration parameter calculating unit, the electro-oculogram change amount signal which is measured when the gaze-point of the user moves from the first calibration index to the second calibration index.

8. The eye gaze tracking apparatus according to claim 7, wherein said calibration parameter calculating unit is configured to determine, as the calibration parameter, a value resulting from dividing the electro-oculogram change amount signal that has been output from said saccade detection unit, by an eyeball movement angle which is measured when the gaze-point of the user moves from the first calibration index to the second calibration index.

9. The eye gaze tracking apparatus according to claim 7, wherein the calibration parameter is a table holding a plurality of combinations of an eyeball movement angle which is measured when the gaze-point of the user moves from the first calibration index to the second calibration index and the electro-oculogram change amount signal that corresponds to the eyeball movement angle.

10. An imaging apparatus which performs imaging in a gaze-path direction of a user, said imaging apparatus comprising:
an imaging unit;
the eye gaze tracking apparatus according to claim 1; and
an image control unit configured to cause said imaging unit to image the gaze-path direction detected by said calibration unit.

11. An eye gaze tracking method for detecting a gaze-path direction of a user from an electro-oculogram, said eye gaze tracking method comprising:
measuring the electro-oculogram resulting from an eye movement, and outputting an electro-oculogram original signal;
presenting a calibration index to the user;
detecting saccadic movements from the electro-oculogram original signal, each of the saccadic movements being a rapid eyeball movement which occurs when a gaze-point of the user moves to the calibration index presented in said presenting of the calibration index;
outputting an electro-oculogram change amount signal based on the detected saccadic movements, the electro-oculogram change amount signal indicating an amount of change, for each of the detected saccadic movements, between (a) a value of the electro-oculogram original signal prior to the detected saccadic movement and (b) a value of the electro-oculogram original signal at a time of the detected saccadic movement, the amount of change indicated by the electro-oculogram change amount signal reflecting a change in potential difference;
calculating a calibration parameter based on a position of the calibration index presented in said presenting of the calibration index and the electro-oculogram change amount signal that has been output in said detecting of the saccadic movement; and
detecting the gaze-path direction of the user from the electro-oculogram original signal based on the calibration parameter.

12. A non-transitory computer-readable recording medium having a program recorded thereon, the program causing a computer to detect a gaze-path direction of a user, the computer being connected to an electro-oculogram measuring unit that measures an electro-oculogram resulting from an eye movement and outputs an electro-oculogram original signal, the program causing the computer to execute a method comprising:
presenting a calibration index to the user;
detecting saccadic movements from the electro-oculogram original signal, each of the saccadic movements being a rapid eyeball movement which occurs when a gaze-point of the user moves to the calibration index presented in said presenting of the calibration index;
outputting an electro-oculogram change amount signal based on the detected saccadic movements, the electro-oculogram change amount signal indicating an amount of change, for each of the detected saccadic movements, between (a) a value of the electro-oculogram original signal prior to the detected saccadic movement and (b) a value of the electro-oculogram original signal at a time of the detected saccadic movement, the amount of change indicated by the electro-oculogram change amount signal reflecting a change in potential difference;
calculating a calibration parameter based on a position of the calibration index presented in said presenting of the calibration index and the electro-oculogram change amount signal that has been output in said detecting of the saccadic movement; and
detecting the gaze-path direction of the user from the electro-oculogram original signal based on the calibration parameter.

13. An integrated circuit which detects a gaze-path direction of a user and is connected to an electro-oculogram measuring unit that measures an electro-oculogram resulting from an eye movement and outputs an electro-oculogram original signal, said integrated circuit comprising:
a calibration index presenting unit configured to present a calibration index to the user;
a saccade detection unit configured to (i) detect saccadic movements from the electro-oculogram original signal, each of the saccadic movements being a rapid eyeball movement which occurs when a gaze-point of the user moves to the calibration index presented by said calibration index presenting unit, and (ii) output an electro-oculogram change amount signal based on the detected saccadic movements, the electro-oculogram change amount signal indicating an amount of change, for each of the detected saccadic movements, between (a) a value of the electro-oculogram original signal prior to the detected saccadic movement and (b) a value of the electro-oculogram original signal at a time of the detected saccadic movement, the amount of change indicated by the electro-oculogram change amount signal reflecting a change in potential difference;
a calibration parameter calculating unit configured to calculate a calibration parameter based on a position of the calibration index presented by said calibration index presenting unit and the electro-oculogram change amount signal that has been output from said saccade detection unit; and
a calibration unit configured to detect the gaze-path direction of the user from the electro-oculogram original signal based on the calibration parameter.

* * * * *